(12) United States Patent
Cunningham et al.

(10) Patent No.: US 7,215,739 B2
(45) Date of Patent: May 8, 2007

(54) ACTIVE DOSE REDUCTION DEVICE AND METHOD

(75) Inventors: James Allan Cunningham, Mississauga (CA); Peter Francis Neysmith, Toronto (CA)

(73) Assignee: Communications & Power Industries Canada Inc., Georgetown (CA)

( * ) Notice: Subject to any disclaimer, the term of this patent is extended or adjusted under 35 U.S.C. 154(b) by 0 days.

(21) Appl. No.: 10/894,427

(22) Filed: Jul. 20, 2004

(65) Prior Publication Data

US 2006/0018430 A1     Jan. 26, 2006

(51) Int. Cl.
*H05G 1/54*     (2006.01)

(52) U.S. Cl. ....................... 378/117; 378/112

(58) Field of Classification Search ........... 378/112, 378/117

See application file for complete search history.

(56) References Cited

U.S. PATENT DOCUMENTS

| | | | |
|---|---|---|---|
| 3,766,391 A * | 10/1973 | Siedband et al. | ........... 378/110 |
| 5,056,125 A | 10/1991 | Beland | |
| 5,077,770 A | 12/1991 | Sammon | |
| 5,388,139 A | 2/1995 | Beland | |
| 5,966,425 A | 10/1999 | Beland | |

FOREIGN PATENT DOCUMENTS

EP     0 819 407 A1     1/1998

* cited by examiner

*Primary Examiner*—Edward J. Glick
*Assistant Examiner*—Thomas R. Artman

(57) ABSTRACT

An active dose radiation device and method decreases the amount of x-rays which may be generated by an x-ray tube following termination of the x-ray exposure. One component of the x-ray system is connected to the device which has a plurality of electronic cells that can be overvoltaged from a first state, where they are less conductive, to a second state, where they are highly conductive. A voltage pulse generator overvoltages a first cell in the plurality of cells at termination of an x-ray exposure. Overvoltaging the first cell causes a cascading effect which eventually overvoltages all of the cells and changes the state of the cells from the first less conductive state to the second highly conductive state. In the second highly conductive state, the cells can conduct current from at least one component of the x-ray system to ground thereby reducing x-rays generated by the x-ray tube and reducing the x-ray dosage from the imaging system after the x-ray exposure has been completed. The plurality of cells automatically reverts to the first state once current passing through the cells decreases below a threshold current level. The plurality of cells are connected to only the anode side 26 or the cathode side 38 of the x-ray imaging device in order to discharge energy from only one side to ground which results in a sufficient decrease in the voltage across the x-ray tube to prevent generation of active dosage of x-rays which may penetrate the patient.

22 Claims, 18 Drawing Sheets

CASE 1
NORMAL OPERATION
OF ADR DEVICE

CASE 1
NORMAL OPERATION
OF ADR DEVICE

CATHODE kV

CASE 2
ABNORMAL OPERATION
OF ADR
HIGH VOLTAGE-SHORT

ADR CURRENT mA

CURRENT AT
WRONG
TIME

502

CASE 2
ABNORMAL OPERATION
OF ADR
HIGH VOLTAGE-SHORT

CASE 3
ABNORMAL OPERATION
OF ADR
ADR FAILED TO
DISCHARGE CABLE

NO CURRENT AT CORRECT TIME

505

CASE 3
ABNORMAL OPERATION
OF ADR
ADR FAILED TO
DISCHARGE CABLE

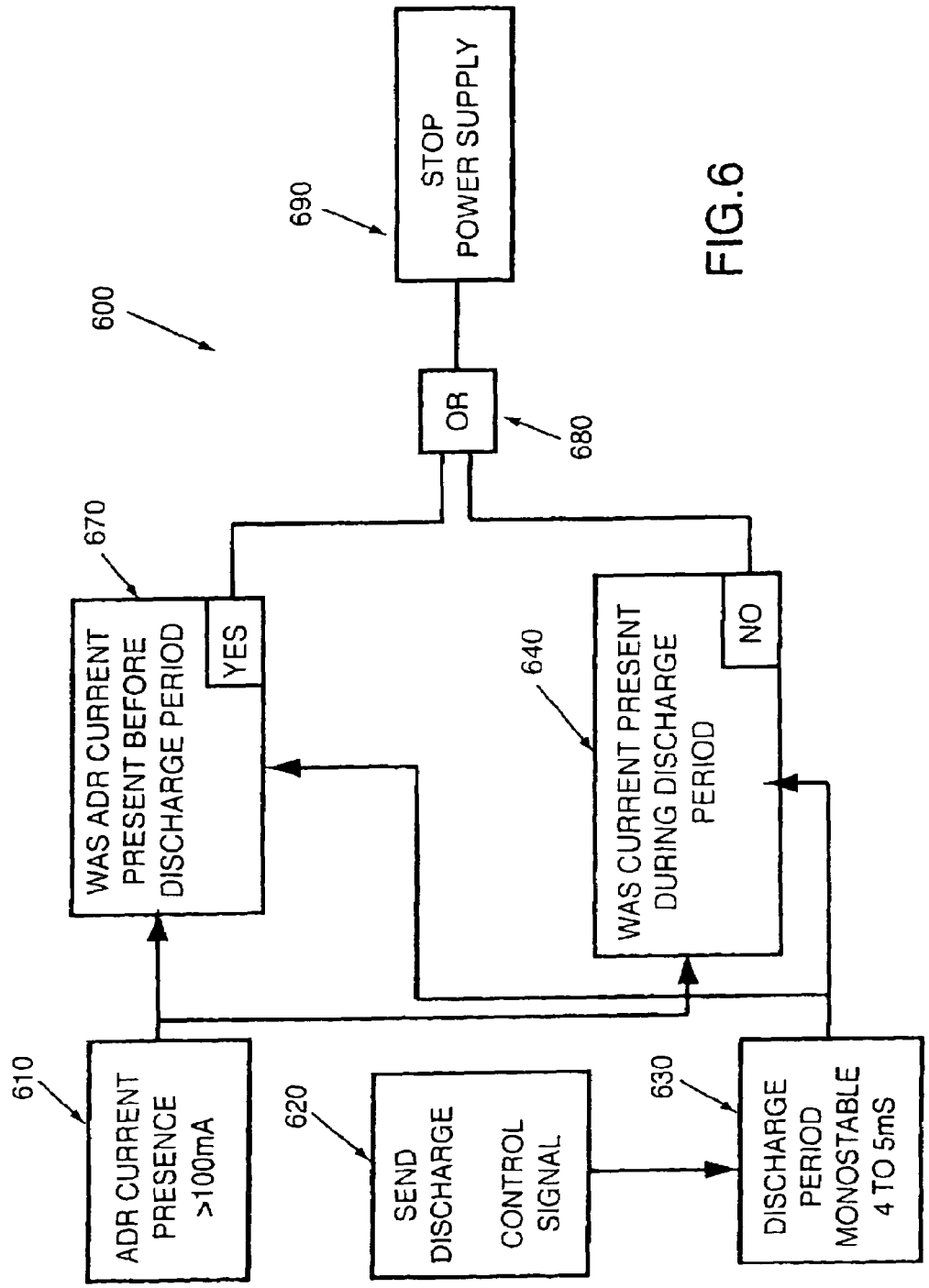

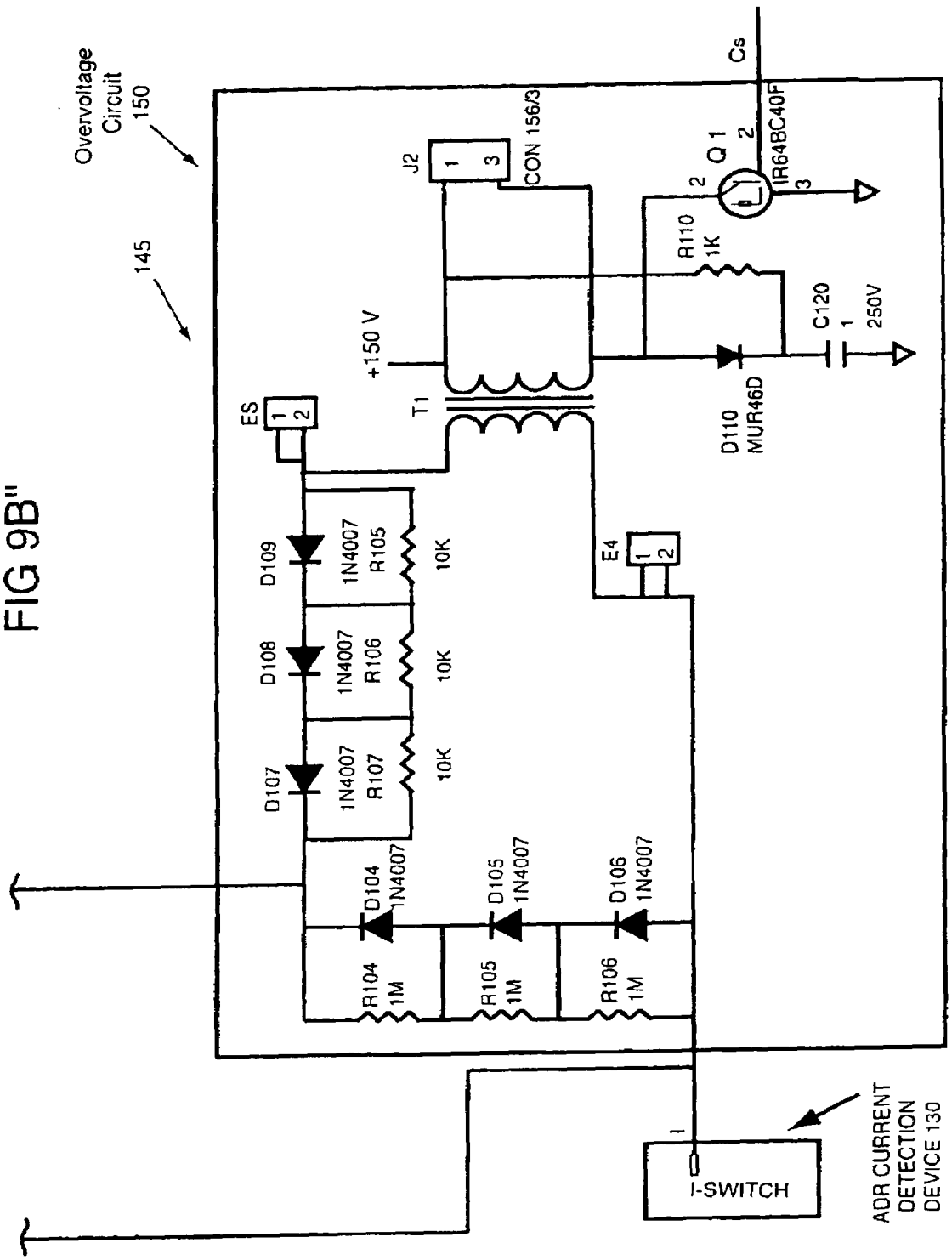
FIG 9B"

ACTIVE DOSE REDUCTION DEVICE AND METHOD

FIELD OF THE INVENTION

The present invention relates in general to a device and method for decreasing the active dosage of x-rays during x-ray imaging. More particularly, the present invention relates to a device and method for reducing excess stored energy, such as stored capacitive energy, from at least some of the components of the x-ray imaging system to reduce the x-ray dosage from the imaging system.

BACKGROUND OF THE INVENTION

During x-ray imaging, x-rays are produced through the generation of electrons by thermionic emission from a cathode, often a tungsten filament, and the acceleration of these electrons within an x-ray tube towards an anode, which causes the emission of x-rays. The emission intensity of the x-rays from the x-ray tube is controlled by the filament current and by the selected voltage potential differential between the anode and the cathode. The selected voltage potential is generally several tens of thousand kilovolts (kV).

There are different types of x-ray imaging known in the art. One type of x-ray imaging, often referred to as radiographic imaging, generally requires a high emission dose from the x-ray tube and is intended for film imaging. Radiographic imaging requires large amounts of x-ray radiation for short periods of exposure time. Another type of x-ray imaging, often referred to as fluoroscopic imaging, generally requires lower emissions from the x-ray tube producing lower amounts of x-ray dose but for longer periods of time. Because of this, fluoroscopic imaging is generally intended for "live" electronic monitoring of the body. This may be done, for example, during a medical procedure when a doctor leads an object through the body and requires continuous imaging of the body and the object in order to properly place the object in the body during the procedure.

Several sub-methods of fluoroscopic imaging have also been used. These may be referred to, in some cases, as continuous (or CW) fluoroscopy, which requires that the x-ray source remain turned on for long periods of time in order to provide "live" electronic monitoring of the body.

With the improvement of imaging techniques, it has been found that short fluoroscopic pulses of x-rays could be detected and held electronically on a monitor and then replaced with a subsequent new image from a further short fluoroscopic pulse of x-rays. This submethod of fluoroscopic imaging, sometimes referred to as pulsed fluoroscopy, has pulses which can vary from a few pulses per second to 30 pulses per second. It is understood that at this rate of pulse fluoroscopy, the intermittent nature of the pulses may not be immediately apparent during the electronic monitoring of the body, or, does not cause a serious degradation to the imaging.

In fluoroscopic imaging, regardless of the specifics of methods used and whether it is continuous or pulsed, the emission from the x-ray tube and the corresponding power level (MA) to the tube is low. This necessitates that the current flowing through the high voltage circuit to the x-ray tube is also low. In these types of situations, when the power supply, also referred to as the generator, stops generating the selected voltage at the termination of an x-ray exposure, whether pulsed fluoroscopy, continuous fluoroscopy or even radiography, a large charge capacitance is left in the components of the imaging system. For example, the system may have a cathode cable extending from the generator to the cathode of the x-ray tube and an anode cable extending from the generator to the anode of the x-ray tube. These cable sets can have a length of typically 50 feet up to 100 feet long. Furthermore, cable sets of sufficient capacity to carry the current and, more importantly, voltage to generate x-rays may have relatively large capacitance between the core and the shield in the cable set, such as in the order of about 50 pico farads (pF) per foot. For cable lengths of 50 to 100 feet, the capacitance of the cable set can be between approximately 2500 pico farads to 5000 pico farads per cable. Using this capacitance and using the simple energy equation of a charged capacitor to emulate the capacitance of the shielded cable, the stored energy in a 50 foot cable can be estimated as:

$$E = \tfrac{1}{2}CV^2 = \tfrac{1}{2}(2500 \times 10^{-12}) \times 62500^2 = 4.9 \text{ joules}$$

when the cable is 50 feet and the voltage at termination is 62.5 kV. The stored capacitive energy will be twice as much if a 100 foot cable is used and there will be an equal amount of energy stored in the anode cable.

Because the x-ray tube during fluoroscopy is generally set to a low emission level for minimal x-ray production, the x-ray tube will not discharge the capacitive energy of the high voltage cables nor the other components in the x-ray system quickly. The fluoroscopic pulsing may then exhibit a "tail" of x-rays that can last into the next pulse. This is illustrated, for instance, by the shaded area 2 in FIG. 1A, which illustrates the potential differential between the anode cable and the cathode cable in conventional x-ray imaging systems. For completeness, FIGS. 1B and 1C, illustrating the voltage differential between the anode cable to ground and the cathode cable to ground, respectively, is also provided.

The "tail" of x-rays is detrimental for several reasons. For instance, the "tail" of x-rays represents excess radiation absorbed dosage to the patient, as well as increased x-ray scatter to others in the vicinity of the patient, including the physician and the assisting staff. Furthermore, the "tail" of x-rays is also detrimental during the x-ray imaging as it generally causes additional detected radiation which is not useful or may have detrimental imaging value because it has a diminishing waveform characteristic. This effect increases exposure time which increases motion artefacts to the displayed image.

Several methods and devices have been used in the past in order to subtract or eliminate the "tail" effect of pulsed fluoroscopic waveforms. One such method involved the use of an x-ray tube which had a third element such as a grid (also referred to as a cathode cup). The grid could be used to turn off the x-rays at high speed by energizing the grid at the appropriate moment. However, grid-type tubes had limited radiographic abilities at higher power levels and at higher voltage thereby limiting grid-type x-ray tubes to lower voltage potentials than non-grid tubes. Another disadvantage of grid-type x-ray tubes is that certain regulatory agencies require a mechanical "flapper" to be added to the x-ray tube port to prevent exposing patients and staff to continuous x-ray should the grid bias be lost. Furthermore, use of the grid-type tubes increased the operating costs of the overall x-ray imaging system because grid-type tubes require a third control line which many systems do not provide and the replacement cost of a grid-type x-ray tube is much higher than non-grid tubes.

Other methods have been considered for eliminating this "tail" effect. For instance, U.S. Pat. No. 5,056,125 to Beland discloses a system having a series of Triac switches connected in series and including discharge resistors and ballasting capacitors. The Triac switches were connected together from both the anode high voltage cable to ground and from the cathode high voltage cable to ground. In addition to having a first connection and a second connection for supporting or conducting the current, the Triac switches also have a third connection, namely a gate, for triggering the switch. The gates in the series of Triac switches were located in the high voltage portion of the apparatus and the Triac switches were activated by a trigger signal which was generated by a low voltage portion of the apparatus. While the Beland device operates relatively well, it suffers from the disadvantage that there is a time lag required for each of the switches to activate gates in the series of switches. Furthermore, there is increased circuitry involved in connecting the three connections of each switch for the number of switches required to support the voltage differential between the cable sets and ground. Furthermore, Beland requires that switches be present to quench the power from both the anode cable and the cathode cable requiring a large number of switches and also requiring that the discharge trigger emanating from the low voltage portion be sent to both the switches connected to the anode cable and the cathode cable.

Another device for discharging a cable set is disclosed in U.S. Pat. No. 5,077,770 to Sammon. The Sammon device utilizes a xenon tube, or a similar high voltage flash tube, or another type of device which has an ionizable material. Sammon discloses that one xenon tube is connected between the anode cable and ground to support the voltage between the anode cable and ground and another xenon tube is connected between the cathode cable and ground to support the voltage between the cathode cable and ground. Sammon discloses that a voltage tickler coil triggers each of the xenon tubes simultaneously in order to ionize the gas in the xenon tube causing the xenon tube to become electrically conductive. While the Sammon device is relatively quick, it suffers from the disadvantage that it requires two xenon tubes which are expensive, must be periodically replaced, and may exhibit changing characteristics over time and use. Also, a relatively large voltage is required to ionize the gas in the xenon tubes increasing the overall cost of operation and the heat generation.

SUMMARY OF THE INVENTION

Accordingly, it is an object of this invention to at least partially overcome the disadvantages of the prior art. Also, it is an object of this invention to provide an improved type of device and method for decreasing the active dosage of x-rays during x-ray imaging.

Accordingly, in one of its aspects, the present invention resides in an x-ray imaging system comprising: an x-ray tube which generates x-rays for x-ray imaging when a pre-selected voltage is supplied thereto; a power supply for supplying power to the x-ray tube at the pre-selected voltage; a cable set comprising an anode cable and a cathode cable for operatively connecting the power supply to the x-ray tube; a plurality of electronic cells, each cell having a first state which prevents flow of current upto a threshold voltage and a second state which permits flow of current, said cells operatively connected to at least one component of the x-ray imaging system, said component selected from the group comprising the x-ray tube, the power supply and the cable set, such that said plurality of cells prevent current flow to ground when in the first state and permit current flow from the at least one component when in the first state and permit current flow from the at least one component when in the second state; an overvoltage circuit to cause at least a first cell of the plurality of electronic cells to exceed the threshold voltage and change from the first state to the second state; and wherein while the power supply supplies power to the x-ray tube at the pre-selected voltage, the cells in the first state prevent current flow from the at least one component, and, upon termination of the power supply supplying power to the x-ray tube at the pre-selected voltage, the overvoltage circuit causes at least the first cell of the plurality of cells to change from the first state to the second state which causes successive cells to change from the first state to the second state to permit current to flow from the at least one component thereby reducing the x-rays generated by the x-ray tube.

In a further aspect, the present invention resides in a device for reducing x-ray dosage from an x-ray imaging system, said device comprising: a plurality of electronic cells, each cell having a first state which prevents flow of current upto a threshold voltage and a second state which permits flow of current, said plurality of electronic cells operatively connected to at least one component of the x-ray imaging system such that, when each of the plurality of cells is in the first state, the voltage differential between across the plurality of cells is insufficient to surpass the threshold voltage of any one cell of the plurality of cells; a voltage pulse source for generating a voltage pulse of sufficient magnitude to cause at least a first cell of the plurality of electronic cells to exceed the threshold voltage; wherein substantially simultaneously with the termination of an x-ray imaging exposure, the voltage pulse source causes a first cell of the plurality of cells to exceed its threshold voltage changing the first cell from the first state to the second state; and wherein the first cell changing from the first state to the second state causes the plurality of cells to change from the first state to the second state permitting discharge of stored energy in the at least one component of the imaging system to ground to reduce the x-ray dosage from the imaging system.

In a still further aspect, the present invention resides a method for reducing an active dose of x-rays during x-ray imaging, said method comprising: applying a pre-selected voltage through a cable set, said cable set including an anode cable and a cathode cable operatively connecting a power supply to an x-ray tube, said pre-selected voltage being sufficient to cause the x-ray tube to generate x-rays for x-ray imaging; upon termination of the pre-selected voltage, over voltaging a first cell of a purality of cells operatively connecting at least one of the cable set or the x-ray tube to ground, each cell in said plurality of cells having a first state which prevents flow of current until overvoltaged and a second state which permits flow of current; wherein over voltaging the first cell of the plurality of cells causes each of the remaining plurality of cells to become overvoltaged whereby stored energy in at least one of the x-ray tube, the anode cable and the cathode cable are discharged to ground thereby decreasing the x-rays generated by the x-ray tube upon termination of the pre-selected voltage.

Accordingly, in one aspect of the present invention, a plurality of cells, each of the cells having a first state, where they prevent the flow of current, and a second state, where they are highly conductive, operatively placed between ground and at least one component of the imaging system in order to assist in discharging the stored capacitive electrical energy from components of the x-ray system to ground at the termination of the x-ray exposure. These cells may change or move from the first state to the second state if they are overvoltaged. The overvoltaging can be performed on a single cell by applying apulse voltage which forces the cell from the first state to the second state. This pulse voltage will then be applied to successive cells until all the cells move from the first state to the second state thereby permitting the conduction of current to ground and discharging the stored energy in the x-ray system. By applying the voltage pulse to a single cell initially, the voltage pulse may have a lower voltage increasing the efficiency and safety and decreasing the cost of the system.

It is understood that as the cells move from the first state to the second state, the voltage across the cells remaining in the first state increases simply because a smaller number of cells must support the selected voltage of the imaging system. Therefore, an advantage of the present system is that once the number of cells in the first state decreases such that the voltage across the cells remaining in the first state exceeds the threshold voltage for overvoltaging the cells, all of the remaining cells will change from the first state to the second state. This can provide a potentially quick cascading effect from overvoltaging an initial cell or cells until all the cells have been overvoltaged and become conductive. Accordingly, this may result in rapid dissipation of stored electrical capacitive energy from the system. Furthermore, because the devices are designed to be overvoltaged, they will not be damaged as a smaller number of cells remain in the first less-conductive state and support the same voltage, improving the resiliency of the system.

Another advantage of the present invention is that the cells, in a further embodiment, will move from the second state, where they are highly conductive, back to the first state where they are less conductive, if the current passing through the cells falls below a threshold current. In this way, once the energy from the x-ray imaging system has been dissipated, and the resulting current passing through the cells decreases below the threshold current, all of the cells will move from the second state back to the first state automatically resetting the cells for the next emission of x-rays of the x-ray imaging system. As such, one potential advantage of the present invention is that it is self-extinguishing and self-regulating in that once the cells move to the second state, they will stay in the second state as long as the energy present in the components of the imaging system can create a current in the cells beyond the threshold current. Once the energy stored in the components of the imaging system dissipates to the point that current passing through the cells decreases below the threshold current, the cells change states from the second state back to the first state in preparation for the next x-ray image. This transition is completed automatically and with minimum control.

A further advantage of the present invention is that, because the transition from the second state to the first state is performed substantially automatically due to the inherent characteristics of the solid state components in the cells, control circuitry is simplified and control reliability increases. Furthermore, the simplification of the control circuitry decreases the overall cost and volume of the device.

Furthermore, it is appreciated that x-rays of low intensity may not be sufficient to enter the patient being imaged. As such, even a reasonable decrease in the potential across the x-ray tube may have a substantial decrease in the x-ray dosage to the patient and staff. Moreover, most x-ray tubes have an attached filter assembly such that a reasonably low energy (kV) x-ray may not be sufficient to penetrate the filter assembly in front of the x-ray tube. While emission of x-rays is a function of a number of variables, it is in particular a function of the voltage differential across the x-ray tube to the exponent 2.3. As such, decreasing the voltage differential across the tube can have a major effect on the x-ray emission from the x-ray tube.

In view of this, it has been appreciated that if the energy can be discharged sufficiently quickly, energy may be discharged through a single device connected to only one component of the x-ray imaging system. For instance, the device may be connected to the anode side or cathode side of the x-ray system, but need not be connected to both. This clearly decreases the overall cost of the system by requiring a single device to be connected only between either the anode side to ground or the cathode side to ground, but not both. The system provides for discharge of the energy from only one side of the x-ray imaging system in part because of the speed of the dissipation of the energy and also because of an appreciation that the voltage differential within the x-ray tube plays a large part in the generation of x-rays.

Accordingly, in a further aspect, the present invention provides an x-ray imaging system having an anode side, which has a positive voltage with respect to ground, and, a cathode side, having a negative voltage with respect to ground, said system comprising an x-ray tube having an anode connected to the anode side and a cathode connected to the cathode side, for generating x-rays at an x-ray energy spectrum with a peak energy level when a voltage differential is applied across the anode and the cathode, said x-ray tube generating x-rays in a diagnostic energy range during an x-ray exposure when a pre-selected voltage is applied across the anode and the cathode; an x-ray filter associated with the x-ray tube to filter x-rays generated by the x-ray tube below the diagnostic energy range; a power supply for supplying power to the x-ray tube at the pre-selected voltage during the x-ray exposure to generate x-rays within the diagnostic energy range; and an active dose reduction device to facilitate reduction of the voltage differential across the anode and cathode by permitting current to flow from one, and only one, of the cathode side or the anode side upon termination of the x-ray exposure such that the voltage differential across the anode and cathode decreases causing the peak energy level to decrease below the diagnostic energy range; wherein upon termination of the x-ray exposure, the active dose reduction device permits current to flow from one, and only one, of the anode side or cathode side to decrease the voltage differential across the anode and cathode such that the peak energy level of the x-rays generated by the x-ray tube is below the diagnostic energy range and substantially filtered by the x-ray filter.

Accordingly, in one preferred embodiment, only the cathode cable connecting the power supply to the cathode of the x-ray tube has a device for dissipating the energy stored in the cable connected thereto to reduce the active dose of x-rays to the patient and the staff in the vicinity of the patient. Such an arrangement has been found to sufficiently quickly discharge the energy from the cathode cable to an extent that the voltage across the x-ray tube has decreased such that a substantial part of the x-rays generated by the stored electrical energy is filtered by the filtering system of the x-ray tube thereby decreasing the active dosage of x-rays to the patient.

In one embodiment, it has been found beneficial to bring the cathode side to ground only for a number of reasons. For instance, x-ray tubes used in typical radiographics imaging and fluoroscopic imaging generally contain a filament housed in a cathode cup or sometimes referred to as a Wehnelt electrode. One purpose of the cathode cup or Wehnelt electrode is that the electrons can be focussed to form a narrow beam in the direction of the anode of the x-ray tube. Unlike normal electronic devices, such as cathode ray tubes, x-ray tubes cannot use magnetic focussing and therefore a cathode cup is a preferred manner of focussing the electrons in an x-ray tube. It is also known that the size of the projected focal spot of the x-ray beam will determine picture resolution by reducing the penumbra effect in the image recording. To accomplish this, a focal spot of 0.3 to 0.6 mm may be used. Thus, focussing a beam can be important in determining picture resolution.

Under fluoroscopic conditions, the filament is kept at a lower power level than in radiographic imaging. Thus, a filament during fluoroscopic conditions will generally be far from being electron limited which could happen with higher x-ray tube currents of greater than 100 mA. This is also referred to as "space charge limited".

Since the space charge "cloud" is greatly influenced by the cathode potential, and as the space charge "cloud" generally forms an electron beam that determines the actual focal spot size for the x-ray tube, it is preferable to turn the space charge cloud to a low potential as quickly as possible so that the residual charge on the anode of the x-ray tube does not alter its size. If the cathode is at some potential, but not completely discharged, when the next x-ray pulse is applied, the initial current flow will cause "focal spot growth" which is not desirable. Thus, it is generally preferred if only one side of the x-ray imaging system is being discharged, to discharge the cathode side rather than the anode side.

Another application for preferring quenching of the cathode side over quenching of the anode side is the ability to provide a cathode focussing bias. This is preferred for magnification applications wherein the normal projected beam is a rectangular projection. For this type of application, the cathode is biased with 100 to 150 vdc to form an iso-lateral beam, thus reducing penumbra effect on the beam width. The ADR device allow for mounting a small bias supply.

In another embodiment, application of the ADR device to quench the cathode to ground allows the ADR device to interface to tri-focus x-ray tubes. An additional filament transformer may be added to the ADR device which will supply the micro-focus spot for fluoroscopy. This is an advantage of quenching the cathode to ground as this cannot generally be done with anode quenching.

A still further advantage of the present invention is its ease to monitor the activity of the device according to one embodiment of the present invention. In particular, the apparatus and method of the present invention leads itself to simple monitoring by having a detection device, which detects the presence of current passing through the cells. If current is detected at the incorrect moment, a fault signal can be sent indicating that a fault has occurred in the x-ray imaging system and/or in the active dose reduction device. Generation of the fault signal will cause the power supply to discontinue supplying power to the x-ray imaging system. In a preferred embodiment, if the fault is only located in the active dose reduction device, the active dose reduction device can be disconnected from the system such that the imaging system can still be used, but without the benefit of the active dose reduction device.

Further aspects of the invention become apparent by reading the following Brief Description of the Drawings and Detailed Description of the Preferred Embodiments which illustrate the invention and preferred embodiments of the invention.

BRIEF DESCRIPTION OF THE DRAWINGS

In the drawings, which illustrate embodiments of the invention:

FIG. 6 illustrates a flow chart used by the ADR device to detect a fault according to one embodiment of the present invention;

DETAILED DESCRIPTION OF THE PREFERRED EMBODIMENTS

Preferred embodiments of the invention and its advantages can be understood by referring to the present drawings. In the present drawings, like numerals are used for like and corresponding parts of the accompanying drawings.

Figure 2:
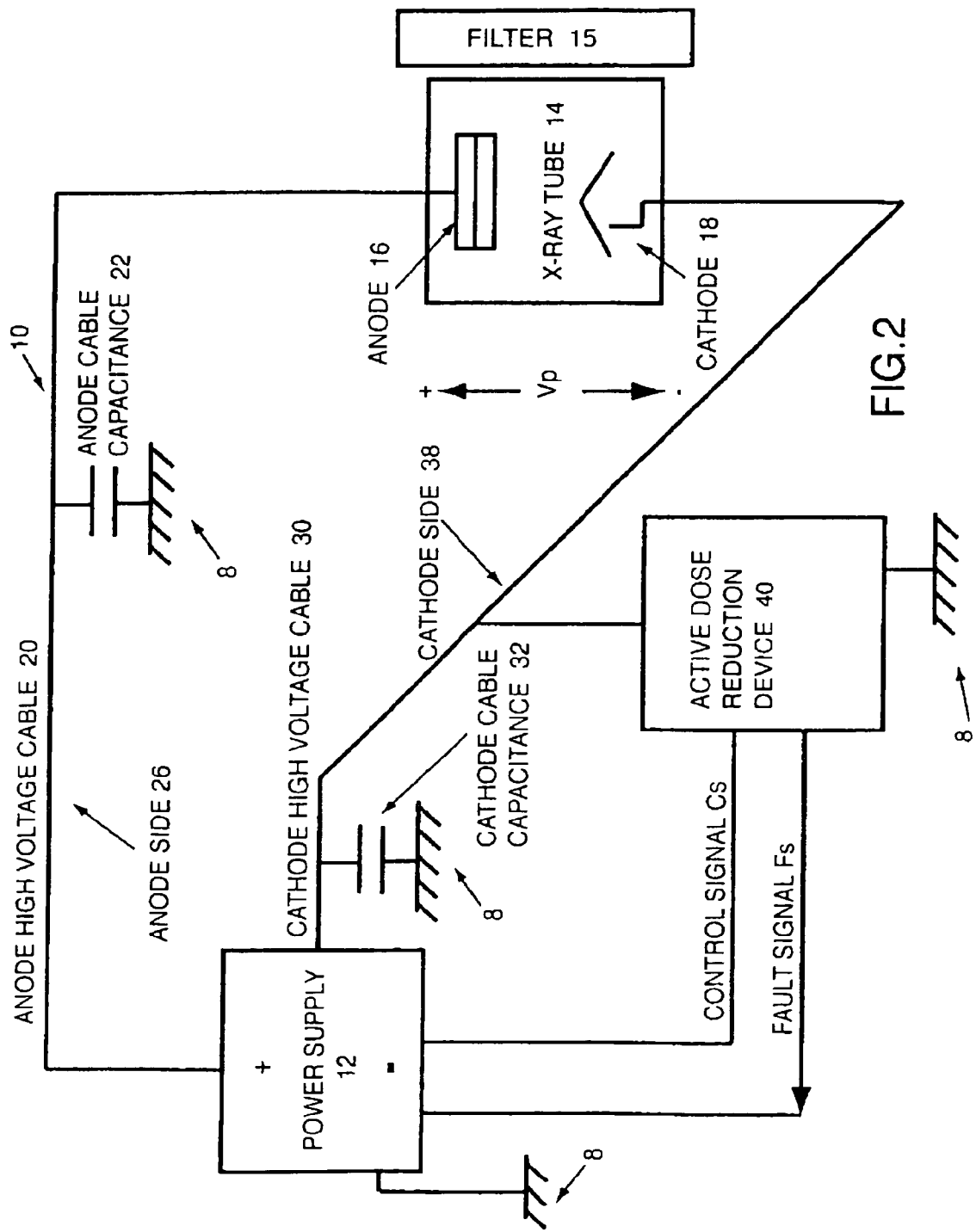
FIG. 2 illustrates a schematic diagram of the present invention according to one embodiment.

FIG. 2 illustrates an imaging system, shown generally by reference numeral 10, comprising an active dose reduction device, shown generally by reference numeral 40, according to one embodiment of the present invention. As illustrated in FIG. 2, the imaging system 10 comprises a power supply 12, such as a generator, for supplying power to an x-ray tube, as shown generally by reference numeral 14, at a preselected voltage Vp. The power supply 12 supplies the power to the x-ray tube 14 through an anode high voltage cable 20, connected to anode 16 of the x-ray tube 14, and a cathode high voltage cable 30, connected to the cathode 18 of the x-ray tube 14. Accordingly, the anode high voltage cable 20 and the cathode high voltage cable 30 represent a cable set which together connect the anode 16 and cathode 18 of the x-ray tube 14 to the anode output and cathode output, respectively, of the power supply 12.

In a preferred embodiment, the x-ray tube 14 will also comprise a filter 15 as illustrated in FIG. 2. The filter 15 is generally a radiation absorption filter which is placed in front of the x-ray tube 14 and intermediate the x-ray tube 14 and the patient. In a preferred embodiment, the x-ray tube 14 will also comprise a Collimator (not shown) which controls the size of the x-ray field. In front or part of the Collimator (not shown) is placed the radiation absorption filter 15.

The anode cable 20 and the cathode cable 30 each generally comprise two conductive leads, one of which is grounded for shielding. While any type of cables 20, 30 may be used, in a preferred embodiment, the cables may comprise EUREKA (trade mark) Pro-Flex high voltage cables manufactured by Progeny Inc. It is understood that the cables may have several tens of thousands of volts and therefore will generally be shielded.

Furthermore, the entire system 10, including the x-ray tube 14 and the generator 12 will generally be connected to a common ground 8. In this way, the anode cable 20 will have a positive voltage with respect to the common ground 8 and the cathode cable 30 will have a negative voltage with respect to the common ground 8. The imaging system 10 may therefore be considered as having an anode side, shown generally by reference numeral 26, having a positive voltage with respect to ground 8, and, a cathode side, shown generally by reference numeral 38, having negative voltage with respect to ground 8. In this way, the preselected voltage Vp applied across the x-ray tube 14 will actually be the combined voltage differential of the positive voltage applied by the anode voltage cable 20 to the anode 16 and the negative voltage applied by the cathode cable 30 to the cathode 18. Typically, the x-ray tube 14 will have a voltage differential of 50 to 80 kV. This will be accomplished by the anode cable 20 having a positive voltage of 25 to 40 kV with respect to ground 8 and the cathode cable 30 having a negative voltage to the cathode 18 of −25 to −40 kV.

During operation, the power supply 12 will supply power at the pre-selected voltage Vp to the x-ray tube 14. The x-ray tube 14 will then generate x-rays for x-ray imaging while the pre-selected voltage Vp is supplied thereto from the generator 12 through the cable sets 20, 30 to the anode 16 and cathode 18 of the x-ray tube 14. At the termination of a particular x-ray exposure, the power supply 12 will discontinue supplying the pre-selected voltage Vp to the x-ray tube. While the pre-selected voltage Vp is being applied, both the anode cable 20 and the cathode cable 30 will have a capacitance, shown generally by reference numerals 22 and 32, respectively, with respect to the common ground 8. The capacitance 22, 32 is indicative of the stored electrical energy in the overall imaging system 10 including the cable sets 20, 30 as well as other components such as the x-ray tube 14 and power supply 12. After the power supply 12 discontinues supplying the pre-selected voltage Vp, the x-ray tube 14 may still generate some x-rays because of the energy stored in the overall imaging system 10, comprising the power supply 12, cable sets 20, 30 and x-ray tube 14 until the stored capacitive energy 22,32 has been discharged.

In order to facilitate discharging of the stored capacitive energy, the system 10 preferably comprises an active dose reduction (ADR) device 40 to permit current flow from at least one component of the imaging system 10 to ground 8 thereby reducing the x-rays generated by the x-ray tube 14 upon termination of the power supply 12 supplying power to the x-ray tube 14 at the pre-selected voltage Vp. The ADR device 40 will generally be triggered in response to a control signal CS indicating termination of an x-ray exposure. In this way, the ADR device 40 will permit current flow to ground 8 from at least one component of the x-ray system 10 upon termination of an x-ray exposure and after the power supply 12 has terminated supplying power to the x-ray tube 14.

It is understood that the control signal CS will generally be supplied upon termination of each x-ray dosage. For instance, during fluoroscopic imaging the control signal CS may be sent every few seconds up to 30 pulses per second, depending on the rate of pulse fluoroscopy. Similarly, in other types of x-ray imaging, the control signal CS will be sent upon termination of an exposure such as when the power supply 12 terminates applying power to the x-ray tube 14 at the pre-selected voltage Vp, and it is desired to dissipate the stored energy in the imaging system 10.

As illustrated in FIG. 2, the ADR reduction device 40 need only be connected to at least one of the components of the imaging system 10, such as the anode high voltage cable 20, the cathode high voltage cable 30, the x-ray tube 14, the power supply 12, or another component of the imaging system 10. In other words, it is not necessary that the ADR device 40 be connected to the anode side 26 and cathode side 38 of the imaging system 10. Rather, it has been found that by discharging the energy stored in either the anode side 26 or the cathode side 38 of the imaging system 10, the voltage across the anode 16 and cathode 18 of the x-ray tube 14 will be decreased sufficiently that the emission level of the x-ray tube 14 will be decreased, thereby decreasing the active dose of x-rays to the patient and staff.

In particular, it has been appreciated that because the x-ray emission from the x-ray tube 14 is a function of the voltage differential between the anode 16 and the cathode 18, it is not necessary to discharge the current from both the anode side 26 and the cathode side 38 of the x-ray tube 14. Rather, by discharging the stored energy from either the anode side 26 or the cathode side 38 sufficiently quickly, there will be a resulting decrease in the x-ray emissions from the x-ray tube 14 because of the decrease in voltage differential across the x-ray tube 14. Furthermore, it has been appreciated that while the emission of x-rays is a function of a number of variables, the emission of x-rays from the x-ray tube 14 is particularly a function of the voltage differential across the x-ray tube to the exponent 2.3. Therefore, a decrease of the overall voltage differential across the x-ray tube 14, regardless of whether this results from a decrease of the voltage between the anode 16 and ground 8 and/or the cathode 18 and ground 8, will result in a reasonable decrease in the voltage differential between the anode 16 and cathode 18 such that the emission of x-rays will decrease.

It has also been appreciated that a reasonable decrease in the emission of x-rays from the x-ray tube 14 will be sufficient to decrease the dosage of the x-rays to the patient. This results, in part, from the fact that x-rays that have been decreased below a certain emission level will not be sufficient to enter the patient, nor will there be substantial scatter to the others within the vicinity of the patient. Therefore, while there may be an ADR device 40 on both the cathode side 38 and anode side 26 of the imaging system 10, it is not necessary to discharge the capacitive energy 22, 32 from both the anode side 26 and the cathode side 38. Rather, a single ADR device 40 may be present between one of the components of the imaging system 10 on the cathode side 38 and ground 8 or one of the components of the imaging system 10 on the anode side 26 and ground 8.

As illustrated in FIG. 2, in a preferred embodiment the imaging system 10 may comprise a single ADR device 40 connecting the cathode side 38 to ground by operatively connecting the cathode cable 30 to ground 8. Nevertheless, if desired, a second ADR device 40 may also be present operatively connecting a component on the anode side 26 of the system 10 to ground 8.

Figure 3:
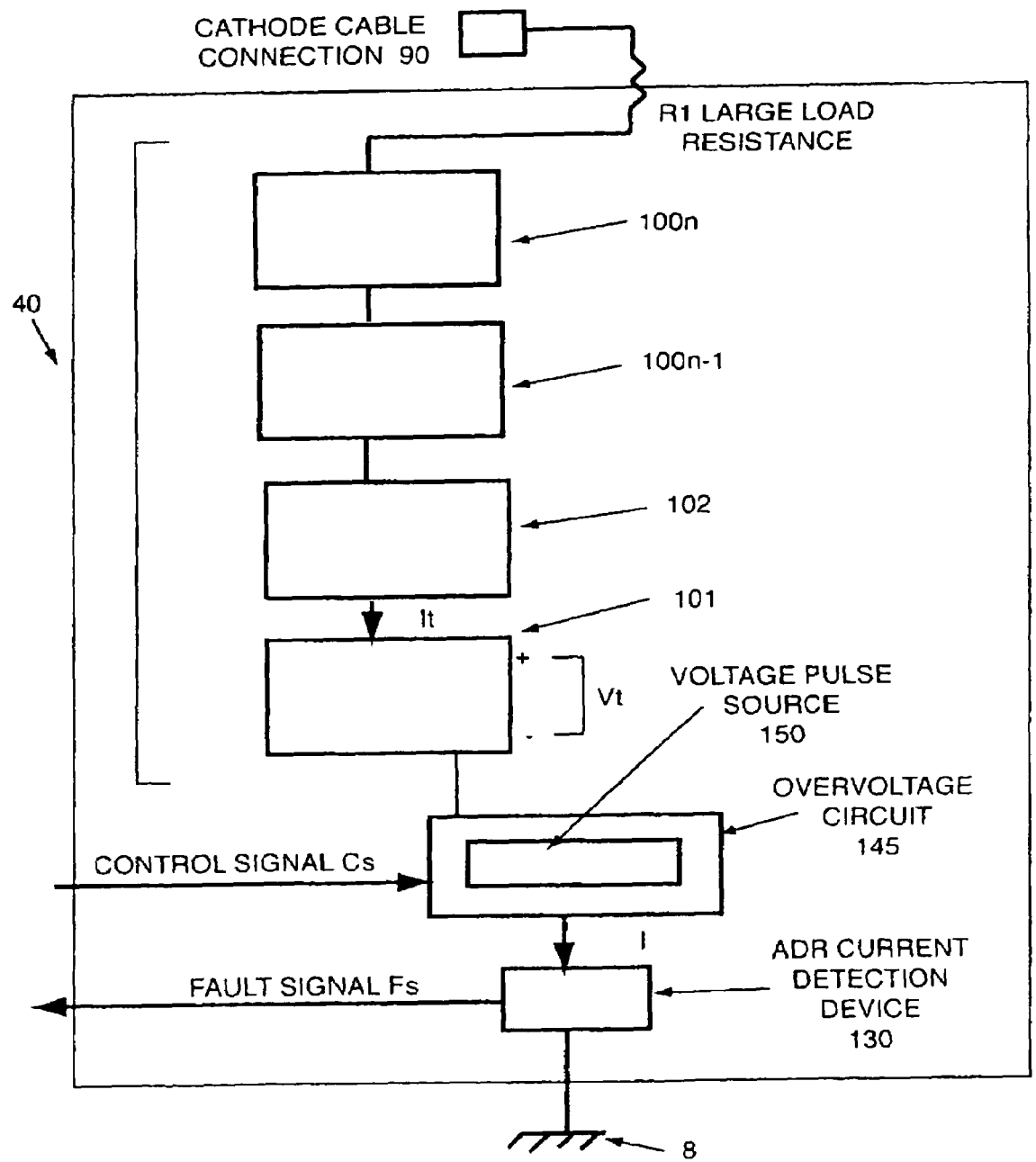
FIG. 3 illustrates a schematic diagram of the active dose reduction device according to one embodiment of the present invention.

FIG. 3 illustrates an ADR device 40 according to a preferred embodiment. As illustrated in FIG. 3 in one embodiment, the ADR device 40 comprises a plurality of electronic cells, as shown collectively by reference numeral 100. For convenience, the plurality of electronic cells 100 may be individually identified as the first cell 101, the second cell 102 up to n cells identified by reference numeral 100 $n$.

Each electronic cell 100 generally has a first state, which prevents flow of current up to a threshold voltage Vt, and a second state, which permits flow of current. The plurality of electronic cells 100, as illustrated in FIG. 3 operatively connect, at least one component of the x-ray imaging system 10 to ground 8. As illustrated in FIG. 3, the plurality of electronic cells 100 may operatively connect the cathode cable 30 through the cathode cable connection 90 to ground 8. However, it is understood that the ADR device 40 may connect any other component of the imaging system 10, including the anode 16, cathode 18, anode cable 20, cathode cable 30 or power supply 12, to ground 8.

The number of electronic cells 100 and their arrangement between the at least one component of the imaging system 10 and ground 8 are preferably selected such that, when each of the plurality of cells 100 is in the first state, the voltage differential between the at least one component of the imaging system 10 and ground 8 is insufficient to surpass the threshold voltage Vt of any one cell 100 of the plurality of cells 100. In other words, the voltage across the at least one component of the x-ray imaging system 10 to ground 8 will be supported by the plurality of electronic cells 100 and will not exceed the threshold voltage Vt for any one electronic cell 100, or at least, will not permit current flow from the at least one component of the imaging system 10 to ground 8.

The plurality of electronic cells 100 may be arranged in any manner and number n which operatively connect the at least one component of the imaging system 10 to ground 8. In a preferred embodiment, the plurality of cells 100 are arranged in a series from the at least one component of the system 10 and ground 8. Furthermore, in a preferred embodiment, the threshold voltage of each cell 100 is approximately 1 kV. In the case where the cathode cable 30 may have a maximum voltage differential to ground 8 of up to 75 kV, then there would need to be at least 75 cells 100 in series to support this voltage differential. In the case of homologation, there would need to be at least sufficient cells 100 to ensure that no one cell 100 would change from the first state to the second even if there is a potential voltage differential of 125%, the maximum voltage differential or roughly 100 kV. In this case, at least 100 cells 100 would be required.

As also illustrated in FIG. 3, the ADR device 40 preferably comprises an overvoltage circuit shown generally by reference numeral 145 in FIG. 3, for generating a voltage of sufficient magnitude to cause at least the first cell, shown generally by reference numeral 101 in FIG. 3, of the plurality of electronic cells 100 to exceed the threshold voltage Vt. The overvoltage circuit 145 may be any type of electronic device which can provide a voltage of sufficient magnitude to cause the first cell 101 to exceed the threshold voltage Vt. Preferably, the overvoltage circuit 145 comprises a voltage pulse source, shown generally by reference numeral 150 in FIG. 3, which generates a voltage pulse of sufficient duration and voltage to overvoltage at least the first cell 100.

It is understood that the voltage pulse generated by the voltage pulse source 150 will be added with the voltage potential across the corresponding cell 100 created by the pre-selected voltage Vt. Therefore, the voltage pulse generated by the voltage pulse source 150 need not necessarily be equal to the threshold voltage Vt, but at the very least the voltage pulse generated by the voltage pulse source 150 when summed with the voltage across the first cell 101 created by the pre-selected voltage Vp must be sufficient to exceed the threshold voltage Vt. To act with caution, in a preferred embodiment, the voltage pulse generated by the voltage pulse source 150 exceeds the threshold voltage Vt for the first cell 101 by 50 to 200% and more preferably 100%. For instance, in a preferred embodiment, the threshold voltage Vt for the first cell 101 will be roughly 1 kV and the voltage pulse generated by the voltage pulse source will be approximately 2 kV. In addition, it is preferred that the voltage pulse source 150 maintain the voltage pulse Vp1 for at least sufficient time for all of the cells 100 to change from the first state to the second state. For instance, in a preferred embodiment, the cells 100 will all change from the first state to the second state in approximately 20 microseconds and the voltage pulse source 150 will generate the voltage pulse for at least 60 to 100 microseconds.

Once the first cell 101 changes from the first state to the second state, the first cell becomes conductive such that any stored energy in the imaging system 10 will be applied to the cells 102 to 100$n$ remaining in the first state. Furthermore, the voltage pulse will commence to act on the second cell 102 once the first cell 101 changes from the first state to the second state. The voltage potential across the first cell 101 created by the pre-selected voltage Vp in combination with the voltage pulse from the voltage pulse generator 150 will cause the second cell 102 to also change from the first state to the second state. Similarly, successive cells 100 will then successively change from the first state to the second state. In this way, the first cell 101 changing from the first state to the second state will cause a cascading effect by the combined application of the voltage pulse Vp1 and the voltage potential across the corresponding cells 100 caused by the pre-selected voltage Vp.

As the number of cells 100 in the first state decreases, the remaining cells 100 remaining in the second state will have an increased voltage thereacross. Once the number of cells remaining in the first state decreases sufficiently, the voltage potential created by the pre-selected voltage Vp across the cells 100 remaining in the first state will increase until it exceeds the threshold voltage Vt of the cells remaining in the first state thereby causing the remaining cells 100 to change from the first state to the second state permitting the flow of current through the cells 100 from the at least one component of the imaging system 10 to ground 8. In this way, current will be permitted to flow from the at least one component of the imaging system 10 to ground 8 reducing the stored capacitive energy in the imaging system 10 and reducing the x-rays generated by the x-ray tube 14.

Once sufficient stored energy in the x-ray imaging system 10 has been discharged, the current passing through the plurality of cells will decrease below a threshold current It. The plurality of cells 100 can change from the second state, in which they are highly conductive, to the first state once the current passing through the plurality of cells decreases below the threshold current It. In this way, once sufficient energy has been discharged from the imaging system 10, the current continuing to pass through the plurality of cells 100 will decrease below the threshold current It thereby causing the cells 100 to change from the second state, where they are highly conductive, to the first state, where they are not highly conductive as long as the voltage remains below the threshold voltage Vt. Thus, the plurality of cells 100 will become re-set so that the plurality of cells 100 can once again prevent current to flow from the at least one component to ground 8. This permits the power supply 12 to again supply power to the x-ray tube 14 at the pre-selected voltage Vp in order to generate x-rays for a subsequent imaging. Thus, the cells 100 can substantially automatically transfer from the second state where they permit current flow back to the first state where they can prevent current flow.

As illustrated in FIG. 3, the plurality of cells 100 are preferably arranged in series between the cathode cable 30 and ground 8. It is understood that the plurality of cells 100 may also be arranged in series between the anode cable 20 and ground 8. For the reasons stated more fully above, it has been appreciated that a single ADR device 40 may be present between the anode cable 20 and ground 8 or the cathode cable 30 and ground 8, but they need not be present between both the anode cable 20 and ground 8 and also the cathode cable 30 and ground 8.

As illustrated in FIG. 3 and also FIG. 2, the voltage pulse may be generated by the voltage pulse source 150 in response to the control signals CS. The control signal CS will be generated by the imaging system 10 and generally by the power supply 12, but not necessarily from the power supply 12. The control signal CS indicates that the most recent x-ray dosage has been terminated and the power supply 12 has terminated supplying power to the x-ray tube 14 at the pre-selected voltage Vp.

Figure 9A:
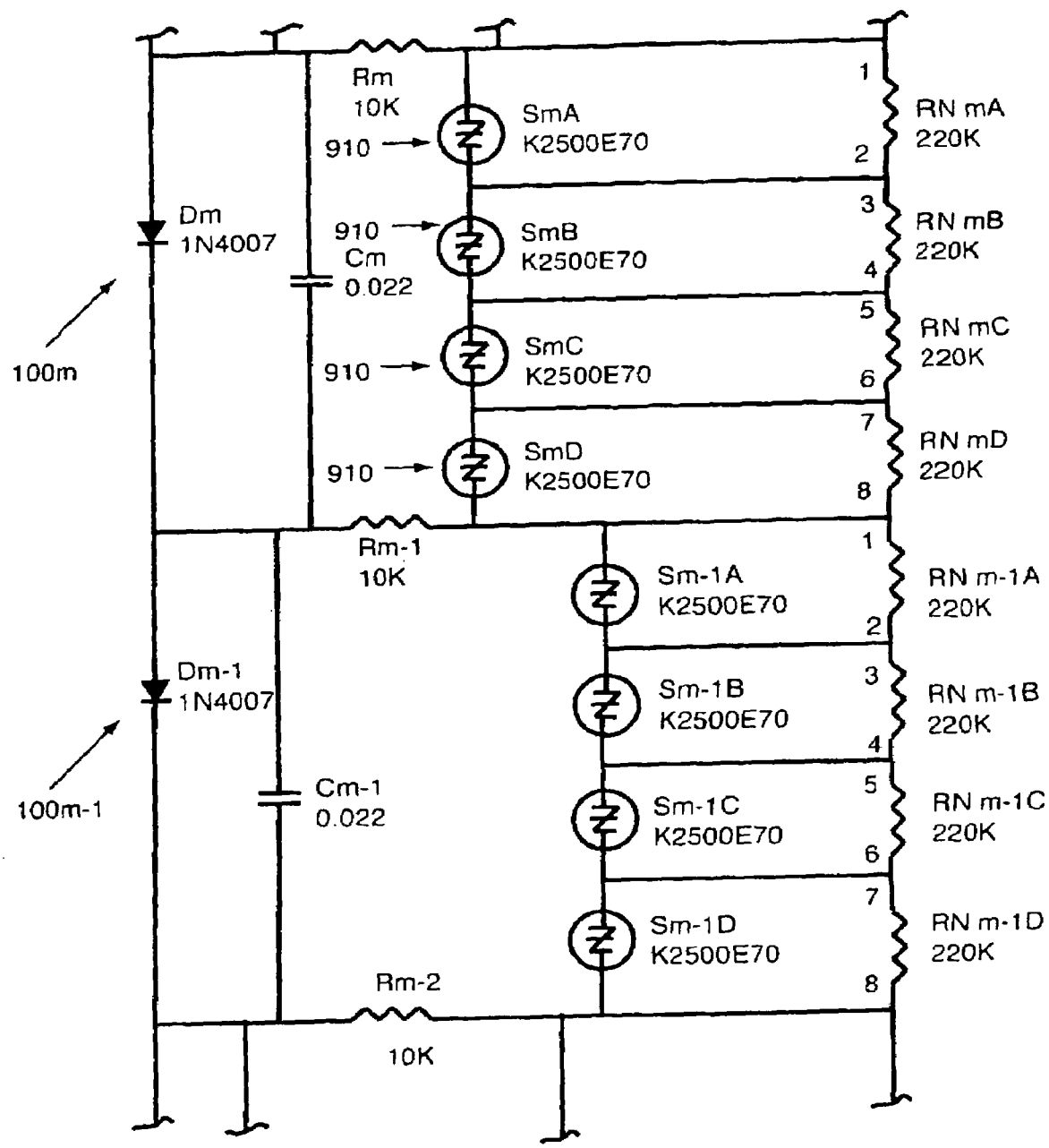
FIGS. 9A, 9B and 9C are more detailed schematic diagrams of an active dose reduction circuit for use in an active dose reduction device according to one embodiment of the present invention.
Figure 9B:
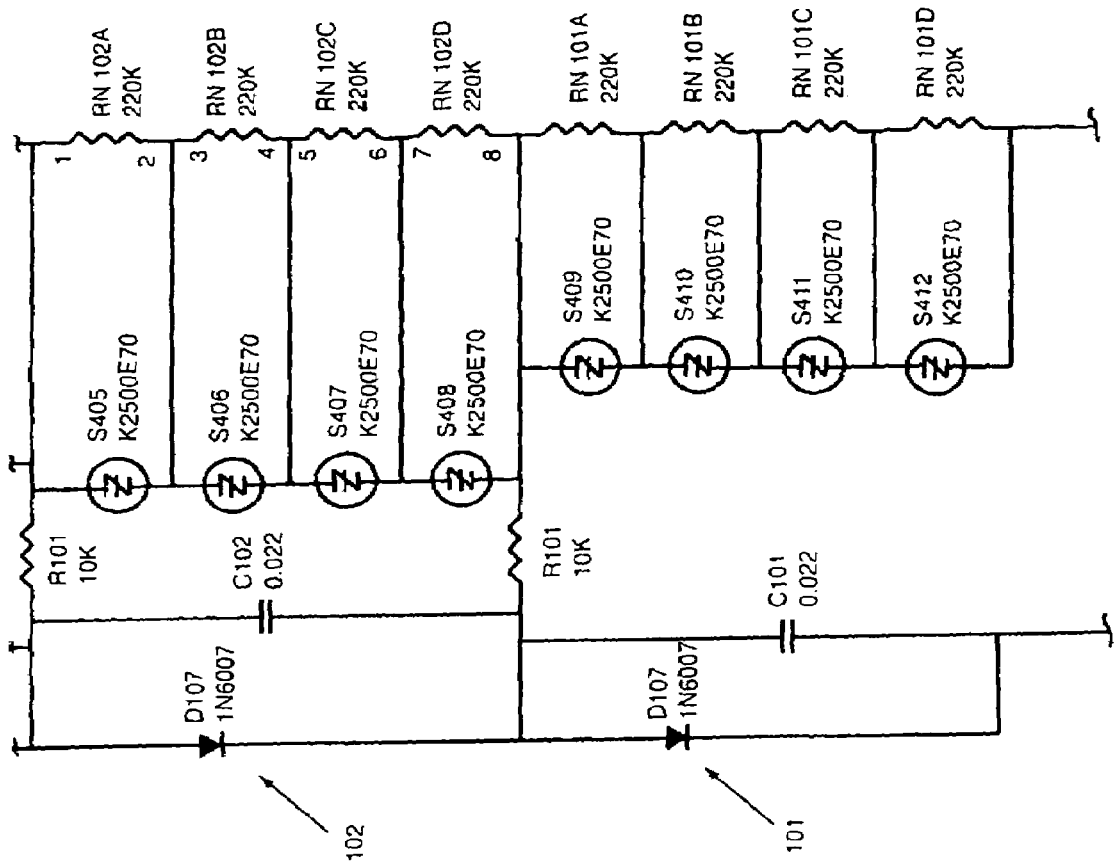

FIG. 9A illustrates an electrical schematic diagram of two cells 100 according to a preferred embodiment. For convenience, the cells 100 illustrated in FIG. 9A are identified as 100$m$ and 100$m$-1 and are two typical cells 100 of a plurality of cells 100. All of the cells 100 of the plurality of cells 100 may have the same configuration, except for the first cell 101, which may have a different configuration as illustrated in FIG. 9B.

As illustrated in FIG. 9A, the cell 100 may comprise a number of electronic overvoltage devices 910. The electronic overvoltage devices 910 are preferably two terminal devices and may comprise silicon control rectifiers. In a preferred embodiment, the overvoltage devices 910 are Sidac devices shown generally by reference Sm. Sidac devices Sm are generally silicon bilateral voltage triggered devices with greater power-handling capabilities than standard diacs. Upon application of a voltage exceeding the Sidac breakover voltage Vo, the Sidac change through a negative resistance region to a low on-state voltage. Conduction continues until the current is interrupted or drops below the minimum holding current of the device. Sidacs may comprise feature glass-passivated junctions to ensure a rugged and dependable device capable of withstanding harsh environments. One Sidac device used in a preferred embodiment of the present invention is manufactured by Treccor located in the United States of America.

Accordingly, in a preferred embodiment, the overvoltage devices 910 have the characteristics similar to those described above with respect to the cells 100. For instance, the Sidac Sm will have a first state in which they are substantially non-conductive up until a Sidac breakover voltage Vo and, when overvoltaged beyond the breakover voltage Vo will electronically change to a second state where they are highly conductive. It is understood that each cell will comprise at least one and likely two or more of the overvoltage devices 910 such that the combined breakover voltage Vo of the overvoltage devices 910 in the cell 100 will equal a threshold voltage Vt of the cell. For instance, the typical cell 100$m$ illustrated in FIG. 9A has four overvoltage devices 910 such that the threshold voltage Vt for the cell 100$m$ illustrated in FIG. 9A will be the sum of the breakover voltage Vo of the four Sidacs 5 mA, SmB, 5 mC and SniD. In a preferred embodiment, where the overvoltage devices 910 are Sidacs having part number K2500E70 manufactured by Treccor, breakdown voltage Vo of each overvoltage device 910 will be approximately 250 volts. In this case, the threshold voltage Vt for the cell 100 having four Sidacs Sn will be approximately four times 250 volts or approximately 1,000 kV.

As also illustrated in FIG. 9A, the cell 100 may comprise a diode Dm, which is designed to ensure that cell 100$m$ does not develop a voltage in an opposite direction. In this case, because the cells 100 as illustrated in FIG. 9A are connected on the cathode side 38 of the imaging system 10, the ADR device 40 will be a negative sysem. In this case, the diode Dm will prevent the cell 100$m$ from becoming positive. It is understood that if the ADR device 40 was connected on the anode side 26, the corresponding diode (not shown) in a cell 100 on the anode side 26 would prevent the cell 100 from becoming negative.

The cell 100$m$ illustrated in FIG. 9A also comprises a capacitor Cm which is designed to maintain the voltage potential across the cell 100 created by the pre-selected voltage Vp. Therefore, the capacitor C in each of the cells 100 is designed to maintain the voltage potential across the corresponding cell 100$m$ created by the pre-selected voltage Vp. In this way, as the cells 100 continue to change from the first state to the second state, the capacitor Cm in each of the other cells 100 will substantially maintain the voltage potential across the corresponding cells 100 created by the pre-selected voltage Vp. This facilitates the cascading effect whereby the overvoltage circuit 145 causing the first cell to change from the first state to the second state causes each of the other cells 100 to successively change from the first state to the second state. Therefore, the capacitor Cm not only holds the voltage potential created by the pre-determined voltage across the cell 100$m$, but also helps to increase the voltage across the cells remaining in the first state to facilitate the cascading effect and electronically change from the remaining cells 100 from the first state to the second state. In a preferred embodiment, the capacitor C is present in each cell 100 as it may allow the voltage pulse Vp1 created by the voltage pulse generator to be smaller and of shorter duration.

It is also noted that the cells comprise a resistor Rm shown to be roughly 10 kilo ohms separating the capacitor Cm and in the overvoltage devices 910. Similarly, another resistor Rm-1 also separates the overvoltage devices 910 and capacitor Cm-1 in cell 100$m$-1. It is understood that the resistor Rm-1 will be shared by the subsequent cell 100$m$-1 in the series. The cell 100$m$ also comprises a resistor network package identified by reference numerals RNmA, RNmB, RNmC and RNmD. It is understood that when the voltage pulse Vp1 is applied to any particular cell 100m, the resistor Rm and the resistor package RNm-1A to RNm-4D form a voltage divider such that almost all of the voltage appears across the resistor package RNmA to RNmD and therefore across the overvoltage devices SmA to SmD. It will be appreciated that the voltage across the overvoltage devices 910 will be cumulative because the overvoltage devices 910 and the preceding cell 100m-1 will have electronically changed to the second state and therefore will be highly conductive. Therefore, the voltage across the overvoltage devices 910 in cell 100m will be a summed voltage, namely the voltage across the capacitor Cm as well as the sum of the voltage across the capacitor Cm-1 times Rm-1 time constant as the capacitor CM-1, as well as the other capacitors located in the preceding cells down to the first cell 101 have not yet been fully discharged. In this way, the voltage across the successive cells 100 in the plurality of cells 100 will become cumulative as more cells 100 change to the second state until this process causes the cells 100 remaining in the first state to change to the second state due to the voltage potential caused by the pre-determined voltage Vp exceeding the threshold voltage Vt of the cells remaining in the first state surpassing the threshold voltage Vt in each case.

FIG. 9B illustrates a schematic diagram of the overvoltage circuit 145 comprising the voltage pulse source 150 according to a preferred embodiment. FIG. 9B also illustrates the first cell 101 and the second cell 102 of the plurality of cells 100. As discussed above, in a preferred embodiment, all of the cells 100 will be substantially the same except for the first cell 101. As illustrated in FIG. 9B, the first cell 101, while having a similar structure to the other cells 100, is connected to the overvoltage circuit 145. In response to the command signal Cs, the overvoltage circuit 145 will generate a voltage sufficient to cause the overvoltage device S409, S410, S411 and S412 in the first cell 101 to change from the first state to the second state. In a preferred embodiment, the overvoltage circuit 145 comprises a transformer T1, which has a ratio of 12 to 1 and can convert the 150 voltage into approximately 1800 volts. The voltage from the transformer T1 will then be applied through the diodes D101 through D109 and the resistors R104 to R109 to the bottom of the resistor network RN101A to RN101D. The resistor network RN101A to RN101D form a voltage divider with the resistor RI01. Because the resistor R101 is 10 kilo ohms in comparison to the resistor RN101A to RN101D which are 220 kilo ohms, when the voltage pulse is generated by the voltage pulse source 150, almost all of the voltage will appear across the resistor network RN101A to RN101D, and therefore across the Sidacs S409, S410, S411 and S412. It is also important to note that the capacitor C103 will also be charged in the same direction as the pulse from the voltage pulse source 104 such that these voltages will be combined across the Sidacs S409, S410, S411 and S412. In this way, the Sidacs S409, S410, S411 and S412 will surpass their breakover voltage Vo and change from the first state to the second state.

Once the Sidacs S409 to S412 change from the first state through to the second state, they will permit the flow of current and essentially act as a short circuit. Thus, the voltage pulse from the overvoltage circuit 145 will then act across the second cell 102. In particular, the overvoltage pulse will now be seen across the resistance divider created by resistor 102 and the resistor network RN102A, RN102B, RN102C and RN102D which will exceed the breakover voltage Vo of Sidacs S405 to S408 in the second cell 102. This will then cause a cascading reaction across the cells 100 remaining in the first state as described above with respect to cells 100m and 100m-1.

The current passing through the plurality of cells 100 preferably passes through a current detection device 130 illustrated in FIG. 9B, FIG. 3 and FIG. 9C and described more fully below.

Figure 4A:
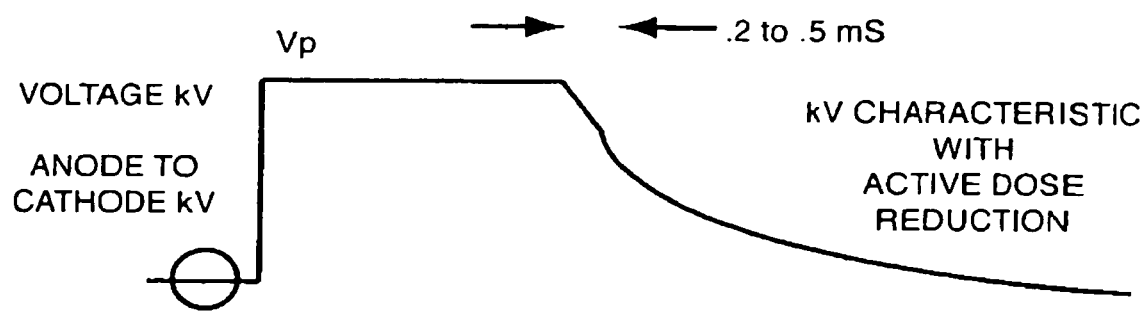
FIGS. 4A, 4B, 4C and 4D illustrate, respectively, the anode to cathode voltage, the anode to ground voltage, the cathode to ground voltage and the discharge command, all with respect to time, during normal operation of the active dose reduction device according to one embodiment of the present invention.
Figure 4B:
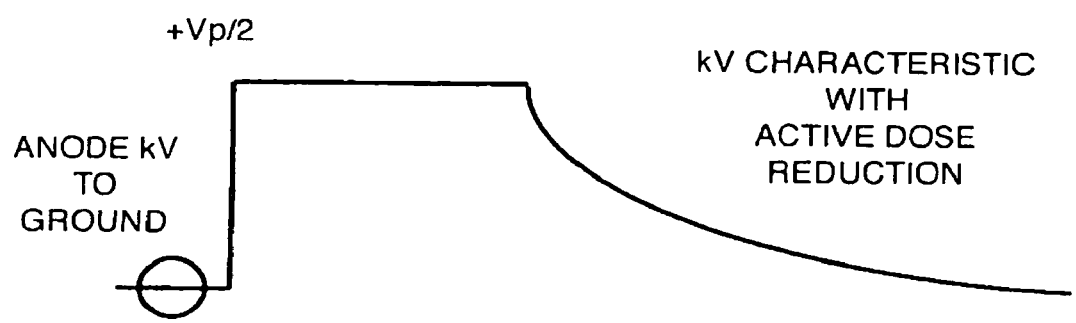
Figure 4C:
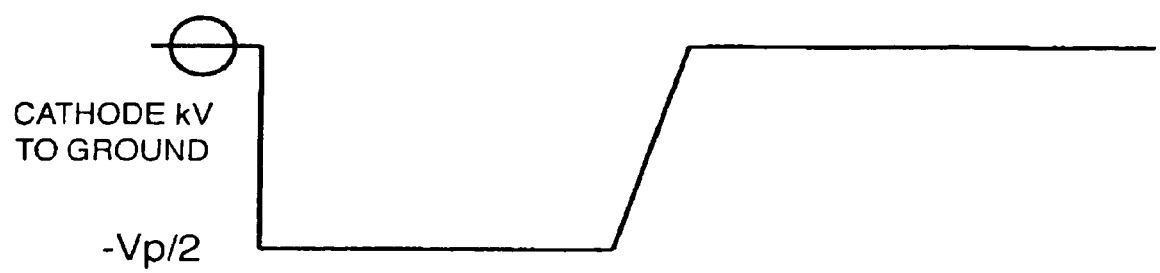
Figure 4D:
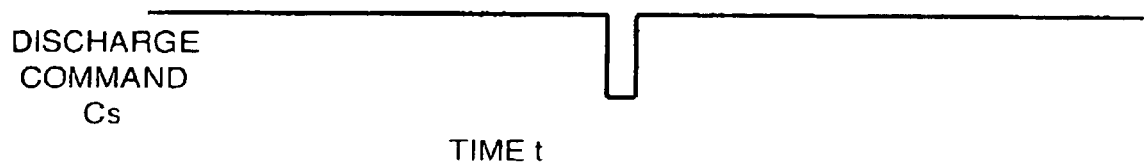

FIGS. 4A, 4B and 4C illustrate, respectively, the anode to cathode voltage, the anode to ground voltage and the cathode to ground voltage, all with respect to time, during normal operation of the active dose reduction device 40 according to one embodiment of the present invention where the active dose reduction device 40 is connected between the cathode side 38 and ground 8 as illustrated for instance in FIG. 2. FIG. 4D illustrates the discharge command Cs which will emanate from the imaging system 10 and generally the power supply 12, in order to initiate the active dose reduction device 40 and in particular the overvoltage circuit 145, which in the preferred embodiment is the voltage pulse source 150, to initiate the overvoltage of the first cell 101.

Prior to the discharge command Cs, the voltage on the anode and cathode is positive and negative Vp/2, indicating that the voltage differential across the x-ray tube 14 is Vp. As illustrated in FIG. 4C, the voltage of the cathode 18, which is negative Vp/2 with respect to ground 8, begins to decrease fairly quickly once the discharge command Cs is received by the ADR device 40. This will result, for instance, once the plurality of cells 100 change from the first state to the second state creating essentially a conductive path to allow current to pass from the cathode side 38 to ground 8. It is noted that the voltage of the anode side 26 with respect to ground 8 will decay in a normal curve similar to the rate of decay shown in FIG. 1B above. This is the case because in this particular embodiment an ADR device 40 is only connected between the cathode side 38 and ground 8 rather than the anode side 26 to ground 8. It is noted that even though voltage is only being discharged from the cathode side 38 by a single ADR device 40, the resulting voltage differential between the anode to the cathode, illustrated in FIG. 4A, undergoes a marked decrease shortly after termination of the exposure, namely 0.2 to 0.5 mS from the discharge command Cs, illustrating that the cathode side 38 is being discharged.

Figure 1A:
FIGS. 1A, 1B and 1C illustrate the anode to cathode, anode to ground and cathode to ground voltages over time, respectively, without active dose reduction according to prior art devices.
Figure 1B:
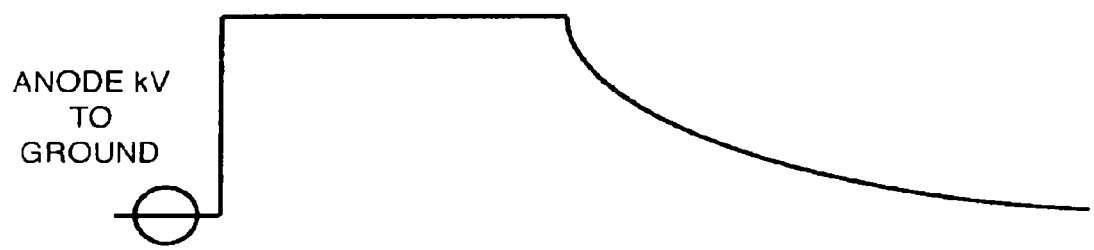
Figure 1C:
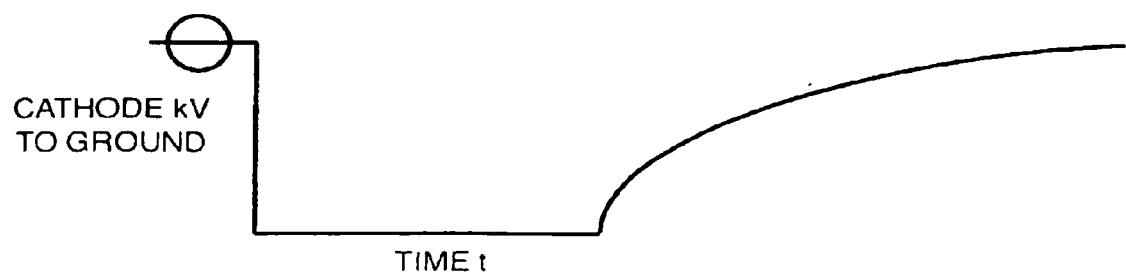

After this period of time, it is noted that the curve illustrated in FIG. 4A returns to the normal decay pattern as shown in FIG. 1A. However, this occurs after a substantial decrease in the voltage differential between the anode side 26 and cathode side 38, corresponding to a voltage decrease between the anode 16 and cathode 18 of the x-ray tube 14. As such, even though there is a fairly steady decaying curve after 0.5 mS and until the anode to ground voltage decreases to substantially 0, because the voltage differential between the anode side 26 and cathode side 38 at this time period has been substantially reduced, the effective active dosage of x-rays to the patient, as well as the scatter radiation to others in the vicinity of the patient, have been greatly decreased. This is the case, at least, because the generation of x-rays is dependent upon the voltage differential between the anode 14 and the cathode 18 to the exponent 2.3 and therefore any rapid decrease in the voltage differential will have a significant decrease in the x-ray dosage being generated by the x-ray tube 14.

Furthermore, many x-ray tubes 14 will generate x-rays in a wide energy spectrum having at least peak energy level within the energy spectrum. For example, diagnostics ranges for x-rays generated by x-ray tubes 14 can be anywhere in the range of 10 to 120 keV. Also, materials used in x-ray tubes 14 will each have characteristic spectrums due to their atomic structure as is well known in the art. For example, when Tungsten is used in an x-ray tube 14, it has its own particular x-ray spectrum which exhibits two characteristic peaks between 55 and 80 kVp. Typically, in radiography the range of diagnostic energies will be between approximately 45 and 150 kVp. In fluoroscopy, the diagnostic range may be between approximately 50 and 125 kV. It is understood that generally x-rays having energy levels below this diagnostic energy range do not contribute to the formation of the x-ray image and therefore are generally not useful.

Furthermore, it should be understood that patient absorption of x-rays is the measurement of the radiation that enters the patient, but does not exit the patient as any photon energy which contributes to the formation of an x-ray image by a detector (not shown). This absorbed x-ray dose is accumulative and may place the patient at risk. Furthermore, operators may be placed at risk due to patient x-ray scatter.

To reduce this unwanted dose to the patient, as well as x-ray scatter filters, such as filter 15 may be placed in front of the x-ray tube 14 as discussed above and illustrated in FIG. 2. In general, the filters 15 may be any type of filters which can filter out some or most of the x-rays which do not contribute to the formation of the x-ray image and/or are outside of the diagnostic energy range of useful x-ray energy levels for a particular imaging system 10 and imaging modality.

In some embodiments, filters 15 may comprise aluminium and/or copper placed within the Collimator (not shown) or just outside the Collimator (not shown). The use of filters 15 may reduce some or most of the radiation outside of the diagnostic energy range, sometimes also referred to as "soft radiation". However, filters tend to be most effective as the kVp of an x-ray tube 14 is reduced. Usually, below 50 kVp, the filters will stop or at least assist in decreasing the emission of low energy x-ray. Since typical fluoroscopy is 80 kVp to 120 kVp, the diagnostic energy range for an x-ray system 10 used in fluoroscopy will generally be above 70 kVp to 120 kVp. As such, a filter 15 which can reduce the emission of low energy rays such as below 50 kVp will have a benefit in reducing patient absorption, scatter in the room and also would eliminate x-ray energy which would not otherwise be effective in producing an image in any event. Furthermore, it has been appreciated that by having a decrease, relatively quickly, of the energy level of the x-rays being generated by the x-ray tube 14, there will be a corresponding significant decrease in the unwanted dose of x-rays to the patient because the filter 15 will stop or reduce the emission of low energy x-rays below the diagnostic energy range even though the system 10 may still have stored energy which is still causing the x-ray tube 14 to generate x-rays. As such, it has been appreciated that having a relatively quick decrease of the voltage differential between the anode 16 and cathode 18 of the x-ray tube 14 such that the x-rays generated by the x-ray tube 14 have a lower energy range will decrease the unwanted x-ray dosage to the patient and have more benefit than the continued decrease of the x-rays generated by the x-ray tube below 50 kVp. As the x-rays generated by the x-ray tube will have an energy spectrum, it is preferred that at least one of the peak energy levels in the x-ray tube be below the diagnostic energy range of the system 10 and within the filtering range of the filter 15 relatively quickly after termination of an x-ray exposure. As indicated above with respect to FIGS. 4A, 4B and 4C, having the voltage difference between the anode 16 and cathode 18 decrease quickly initially such as 0.2 to 0.5 ms as illustrated, for instance, in FIGS. 4A, 4B and 4C, will have a significant effect on decreasing the patient dosage. This is the case even though one side, such as the anode side 26 decays slower than the cathode side 38 because the active dose reduction device 40 is only connected to the cathode side 38. In other words, having a significant and quick decrease in the peak energy level of the x-rays generated by the x-ray tube 14 to below the diagnostic energy range and preferably within the filtering capabilities of the filter 15 by decreasing the voltage differential between the anode 16 and cathode 18 of the x-ray tube 14, will have a significant reduction in the patient dosage.

Accordingly, by discharging at least one side 26, 38 of the x-ray system 10, the resulting x-rays being generated will be sufficiently low such as to decrease the amount of x-rays being emitted from the x-ray tube 14, and, the filter 15 of the x-ray tube 14 may better filter the lower energy x-rays decreasing the x-ray dosage to the patient even though the other side 38, 22 of the system 10 will be left to discharge without the use of an ADR device 40. Nevertheless, it is understood that an ADR device 40 may be connected so as to discharge both the anode side 26 and the cathode side 38 of the imaging system 10. In this case, the curve for the anode to ground illustrated in FIG. 4B will be similar to the curve for the cathode to ground illustrated in FIG. 4C. The resulting anode to cathode voltage illustrated in FIG. 4A will then be a much straighter line with little or no decay directly from the pre-selected voltage Vp.

Figure 8A:
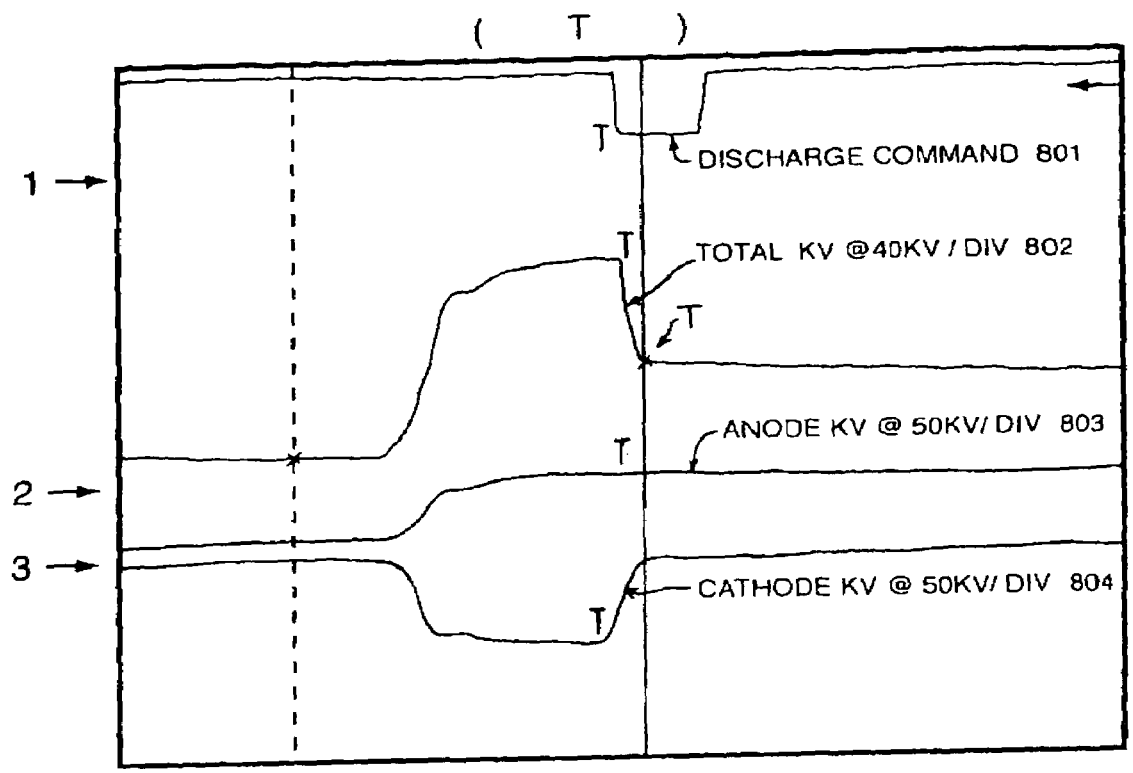
FIGS. 8A and 8B illustrate the discharge command total voltage, anode voltage and cathode voltage over time with each demarcation representing 1 millisecond (FIG. 8A) and 10 milliseconds (FIG. 8B) when cable discharge occurs according to one embodiment of the present invention.
Figure 8B:
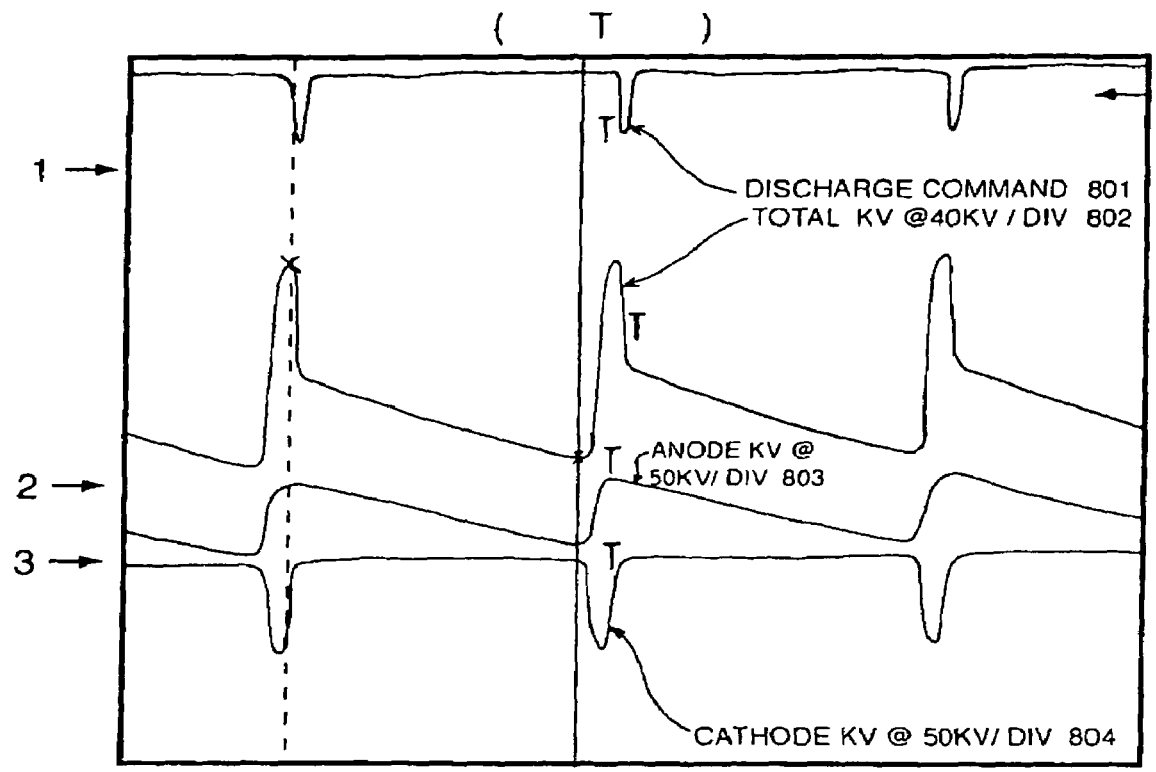

FIGS. 8A and 8B are a set of oscillographs, each oscillograph depicting the discharge command (identified by curve 801), the total kV differential between the anode 16 and the cathode 18 of the x-ray tube 14 (identified by curve 802), the anode kVs to ground 8 (identified by curve 803) and the cathode kVs to ground 8 (identified by curve 804). FIG. 8A illustrates the oscillograph at 1mS per division (representing a close up) of FIG. 8B, which is at 10 mS per division, FIGS. 8A and 8B represent experimental outputs using an ADR device 40 as described above according to a preferred embodiment of the present invention with a single ADR device 40 connected only between the cathode side 38 and ground 8.

As illustrated in FIG. 8A, the cathode curve 804 decreases quickly once the discharge command Cs has been received by the ADR device 40. By contrast, the anode curve 803 shows a much lower rate of decay which is consistent with prior art devices as would be expected because no ADR device 40 is connected to the anode side 26 in this embodiment. Nevertheless, the resulting total voltage differential shows a marked decrease once the discharge command Cs (and curve 801) is received representing the decrease in the cathode to ground voltage (curve 804) even though the anode to ground voltage (curve 803) is still relatively high.

It is understood that curves 802, 803 and 804 are empirical results consistent with the curves illustrated in FIGS. 4A, 4B and 4C, respectively. FIGS. 8A and 8B also illustrate how discharging only one side of the imaging system 10, in this preferred embodiment the cathode side 38, using a single ADR device 40 is sufficient to decrease the voltage differential across the anode 16 and cathode 18 and the x-ray tube 14 such as to decrease the x-ray dosage to the patient even though the anode side 26 is not being discharged. As discussed above, instead of the ADR device 40 being connected to the cathode side 38, the ADR device 40 could have been connected to the anode side 26 in which case the anode curve 803 and cathode curve 804 would be substantially interchanged. It is also understood that the device 10 could comprise two ADR devices 40, one connecting the anode side 26 to ground 8 and the other connecting the cathode side 38 to ground 8. In this embodiment, both the anode and cathode curve would have the shape illustrated by curve 804. The total voltage differential between the anode and cathode, illustrated by curve 802, would accordingly differ, particularly after the point T in FIG. 8A.

Figure 7A:
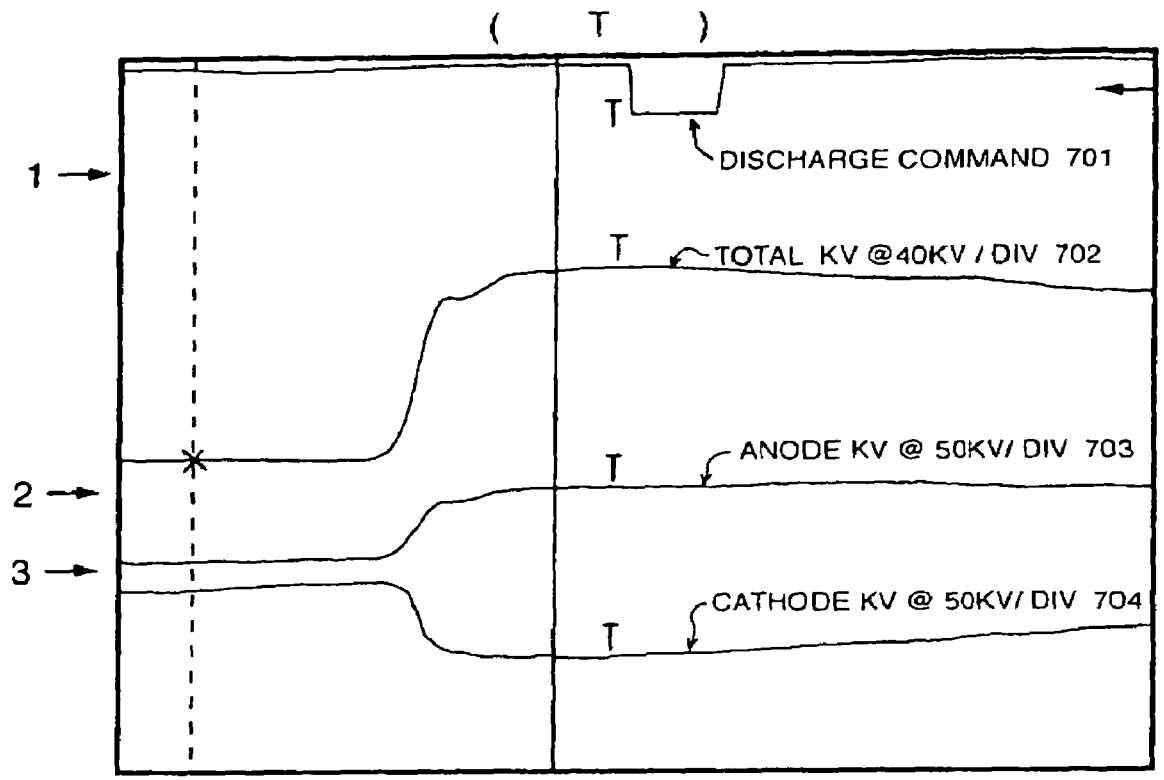
FIGS. 7A and 7B illustrate the discharge command total voltage, anode voltage and cathode voltage over time with each demarcation representing 1 millisecond (FIG. 7A) and 10 milliseconds (FIG. 7B) when no cable discharge occurs according to one embodiment of the present invention.
Figure 7B:
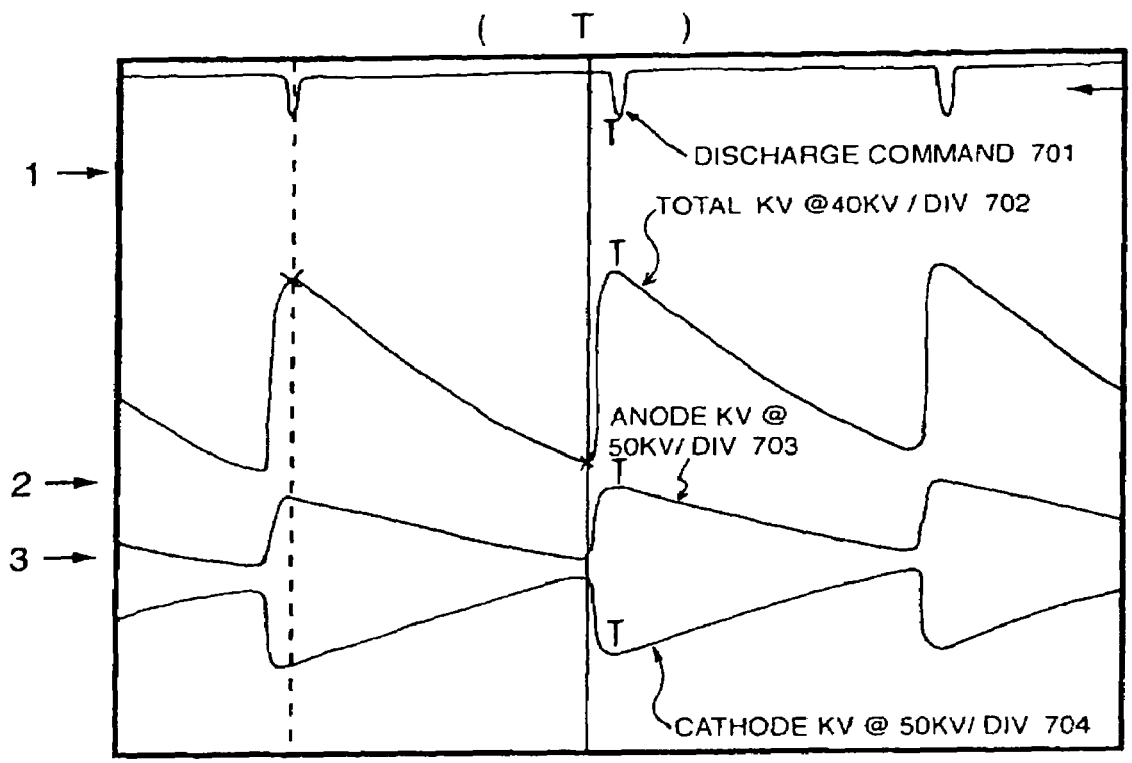

By comparison, FIGS. 7A and 7B illustrate a set of oscillographs depicting the discharge command (curve 701), the total kV difference between anode and cathode (curve 702), the anode to ground voltage (curve 703) and the cathode to ground voltage (curve 704) all respect to time. FIG. 7A illustrates an oscillograph at 1 mS per division and FIG. 7B illustrates the oscillograph at 10 mS per division. FIGS. 7A and 7B illustrate the embodiment where the same system illustrated in FIG. 2 has a discharge command 701, but there is no ADR device 40 operating. In otherwords, FIGS. 7A and 7B illustrate the prior art system, or, the system illustrated in FIG. 2 in the ADR device 40 is not operating properly. It is understood that the system illustrated in FIG. 2 may optionally operate without the ADR device 40, such as if the ADR device 40 is malfunctioning. In this case, the system 10 would have discharge characteristics similar to those of the prior art devices as also illustrated in FIGS. 7A and 7B. In order to detect potential malfunctions in the ADR device 40, the ADR device 40 comprises an ADR current detection device, shown generally by reference numeral 130 in FIG. 3.

As illustrated in FIG. 3, the ADR detection device 130 detects the presence of current I passing through the plurality of cells 100. If current I is present at the incorrect time, the ADR detection device 130 will generate a fault signal Fs, which may be received by any component in the imaging system 10, but preferably will be received by the power supply 12. Receipt of the fault signal Fs, indicates that the ADR device 40 is not operating and imaging will be temporarily discontinued. Optionally, the operator of the imaging system 10 may continue to use the imaging system 10, but without the ADR device 40. In this case, the voltage characteristics of the imaging device 10 will no longer appear as illustrated in FIGS. 8A and 8B, but rather will appear as illustrated in FIGS. 7A and 7B. The system 10 can still operate, but with a corresponding increase in the x-ray dosage due to the slower discharge of the energy stored in the imaging device 10.

According to one preferred embodiment of the present invention, FIG. 6 illustrates a fault detection block diagram shown generally by reference numeral 600. As illustrated in FIG. 6, the ADR current detection device 130 will detect the presence of current at step 610. It is understood that the step 610 need not detect the magnitude of the current I, but only if the current is present. The threshold value of 100 mA may be used in order to signify the presence of current I, however, any other threshold value may be optionally used.

The discharge period is shown as commencing at step 630 for a period of 4 to 5 mS in response to the discharge control signal Cs being sent at step 620. In step 670, if the ADR current I is present before the discharge period, then this would indicate that the cells 100 have improperly changed from the first state to the second state permitting the flow of current before the discharge period has commenced. An indication of a yes in step 670 will cause a signal to be sent through the OR function at step 680 to stop the generator, namely the power supply 12 at step 690.

During the discharge period, as shown by step 640 current should be present. However, an indication of no current present during the discharge period in step 640 will cause a signal to be sent through the OR function at step 680 to stop the power supply 12. It is understood that the power supply 12 will be stopped at step 690 by the generation of the fault signal Fs which will be sent either directly or indirectly to the power supply 12. Accordingly, as illustrated by the block diagram 600 of FIG. 6, the fault signal Fs will be generated if the ADR current I is present before the discharge period commences (step 670), or, if the ADR current I is not present during the discharge period (step 640).

Figure 5A:
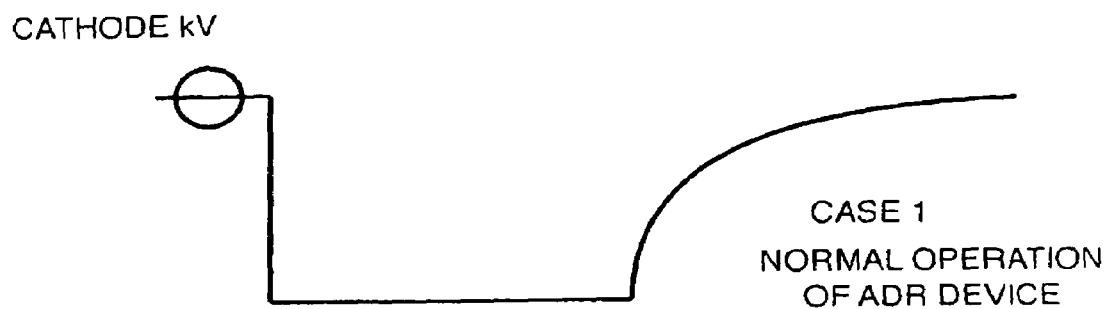
FIGS. 5A and 5B illustrate the cathode voltage to time and the current to time, respectively, during normal operation of the ADR circuit and the ADR device according to one embodiment of the present invention.
Figure 5B:
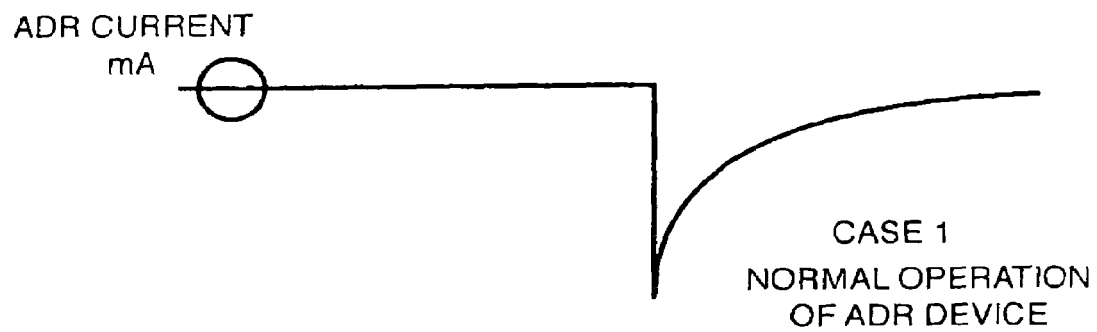

FIGS. 5A and 5B illustrate case 1, the normal operation of the ADR device 40. In particular, FIG. 5A illustrates the fairly rapid decrease of the cathode voltage and the presence of the ADR current I at approximately the same time. This is consistent with the normal operation of the ADR device 40.

Figure 5C:
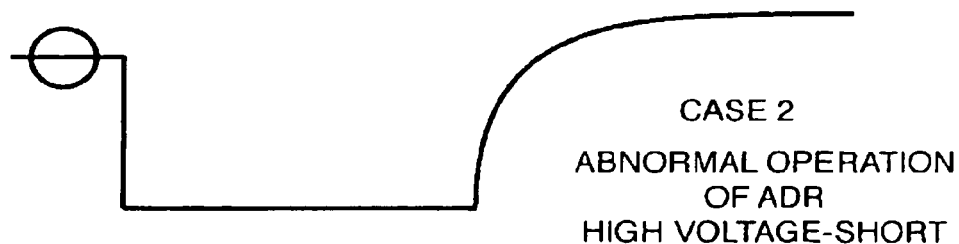
FIGS. 5C and 5D illustrate the cathode voltage and ADR current, respectively, during abnormal operation of the ADR device when a high voltage short has occurred.
Figure 5D:

FIGS. 5C and 5D illustrate case 2, the abnormal operation of the ADR device when there is an ADR current at the wrong time, identified by reference numeral 502. This is consistent with a yes at step 670. As illustrated by FIG. 5D, the ADR current I will be fairly significant before the discharge period because the power supply 12 is supplying power and then will commence to decrease as the cathode voltage illustrated in FIG. 5C also decreases.

Figure 5E:
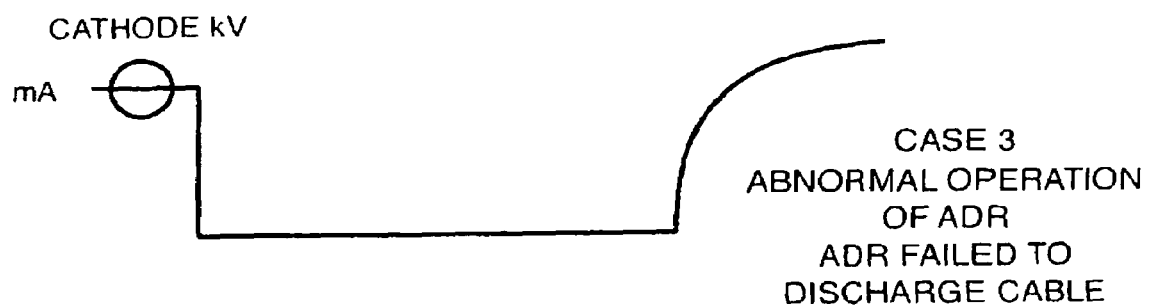
FIGS. 5E and 5F illustrate the cathode voltage and the ADR current, respective, over time during the abnormal operation of the ADR when the ADR failed to discharge the cable.
Figure 5F:
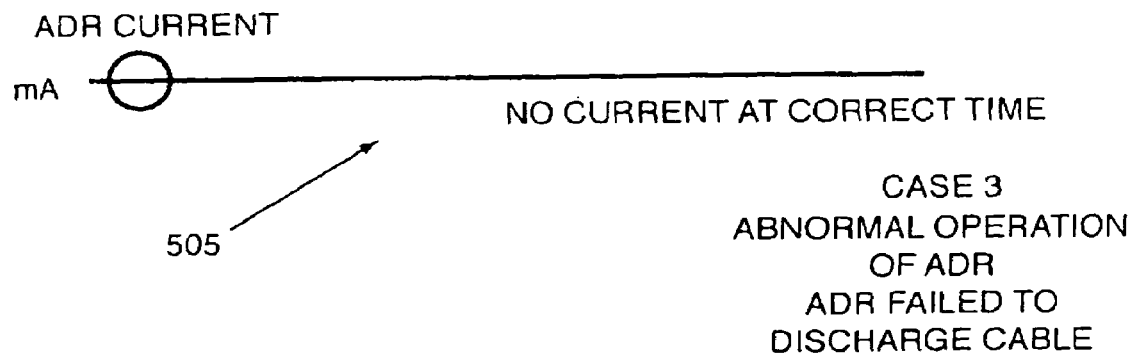

FIGS. 5A, 5E and 5F illustrate case 3, the abnormal operation of the ADR device when the ADR devices fail to discharge at least one component of the imaging system 10, in this case the cathode cable 30. As illustrated by reference numeral 505 and the dotted line, there is no current at the correct time, namely when the discharge period commences. This is consistent with no current present during the discharge period as shown in step 640.

Accordingly, FIGS. 5C and 5D illustrate the case 2 abnormal operation of the ADR device when the ADR current I is present before the discharge period, corresponding no in step 670, and FIGS. 5E and 5F illustrate the case 3 abnormal operation of ADR device when the ADR has failed to discharge the cable during the discharge period, corresponding to no in step 640. FIGS. 5A and 5B illustrate the case 1 normal operation of the ADR device 40.

Figure 9C:
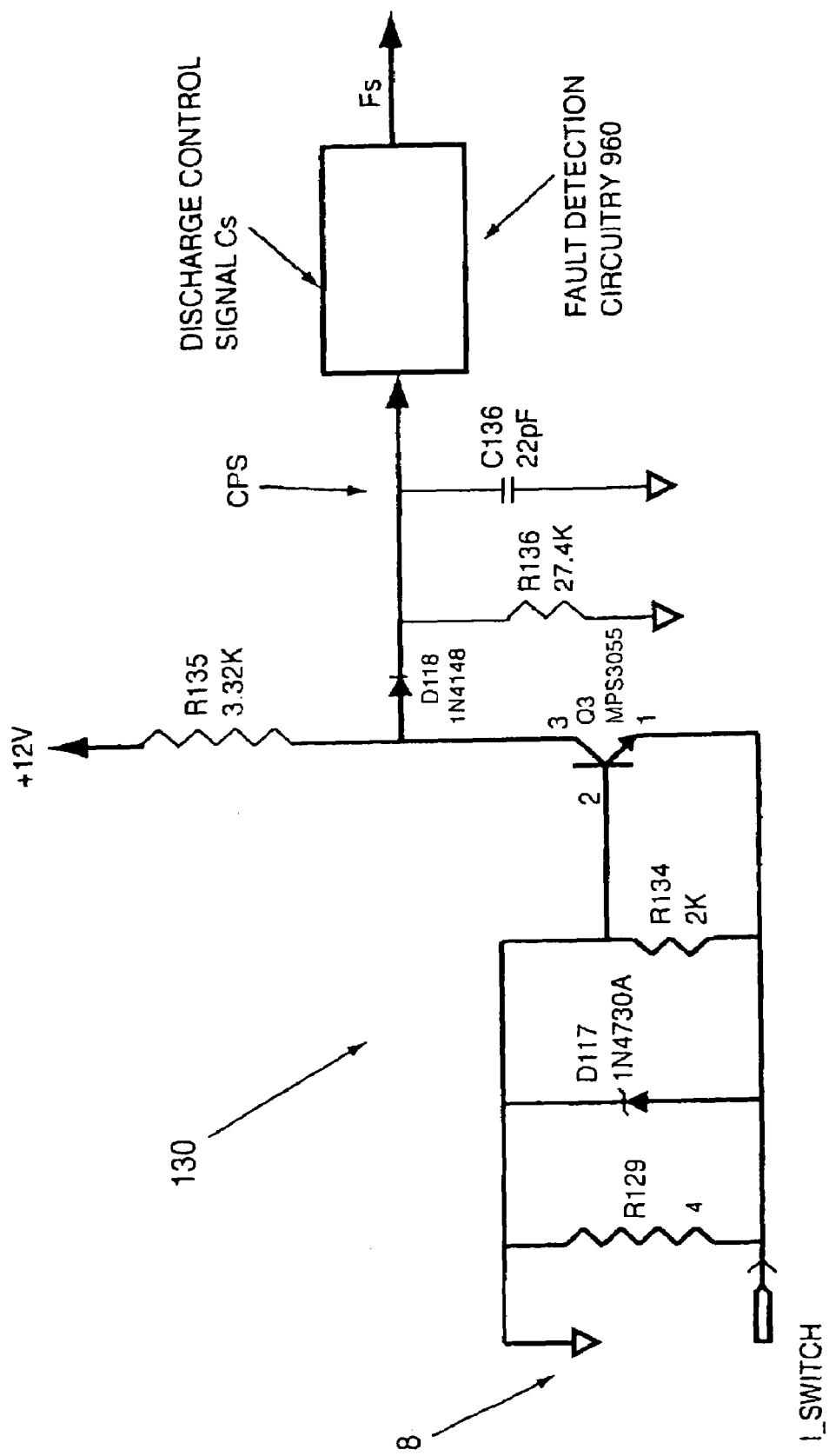

FIG. 9C illustrates a preferred embodiment of the ADR current detection device 130. As illustrated in FIG. 9C, the current I from the plurality of cells 100 will pass through a resistor R129. Preferably the resistor 129 has a resistance of 4 ohms. The current I will then pass to ground 8. The presence of the current I will then be detected by a combination of diode 117, resistors R134, R129 and transistor Q3 which generates a current present signal CPS which is received across resistor R136 and capacitor C136 by the fault detection circuitry 960. The fault detection circuitry 960 also preferably receives the discharge control signal Cs in order to determine when the discharge period commences. The fault detection circuitry 960 implements the fault detection block diagram 600 illustrated in FIG. 6 and discussed more fully above. It is also understood that the fault detection circuitry 960 may be any combination of hardware and/or software in order to implement the fault detection block diagram 600. It is understood that the ADR current I need not be all of the current from all of the cells 100, but rather the current from at least one cell 100 of the plurality of the cells 100. In other words, the ADR current I need only be a portion of the current passing through the plurality of cells 100 from the at least one component of the imaging system 10 to ground 8. This is the case at least because the fault detection circuitry 960 preferably detects only the presence of the ADR current I rather than the value of the ADR current I.

Figure 10:
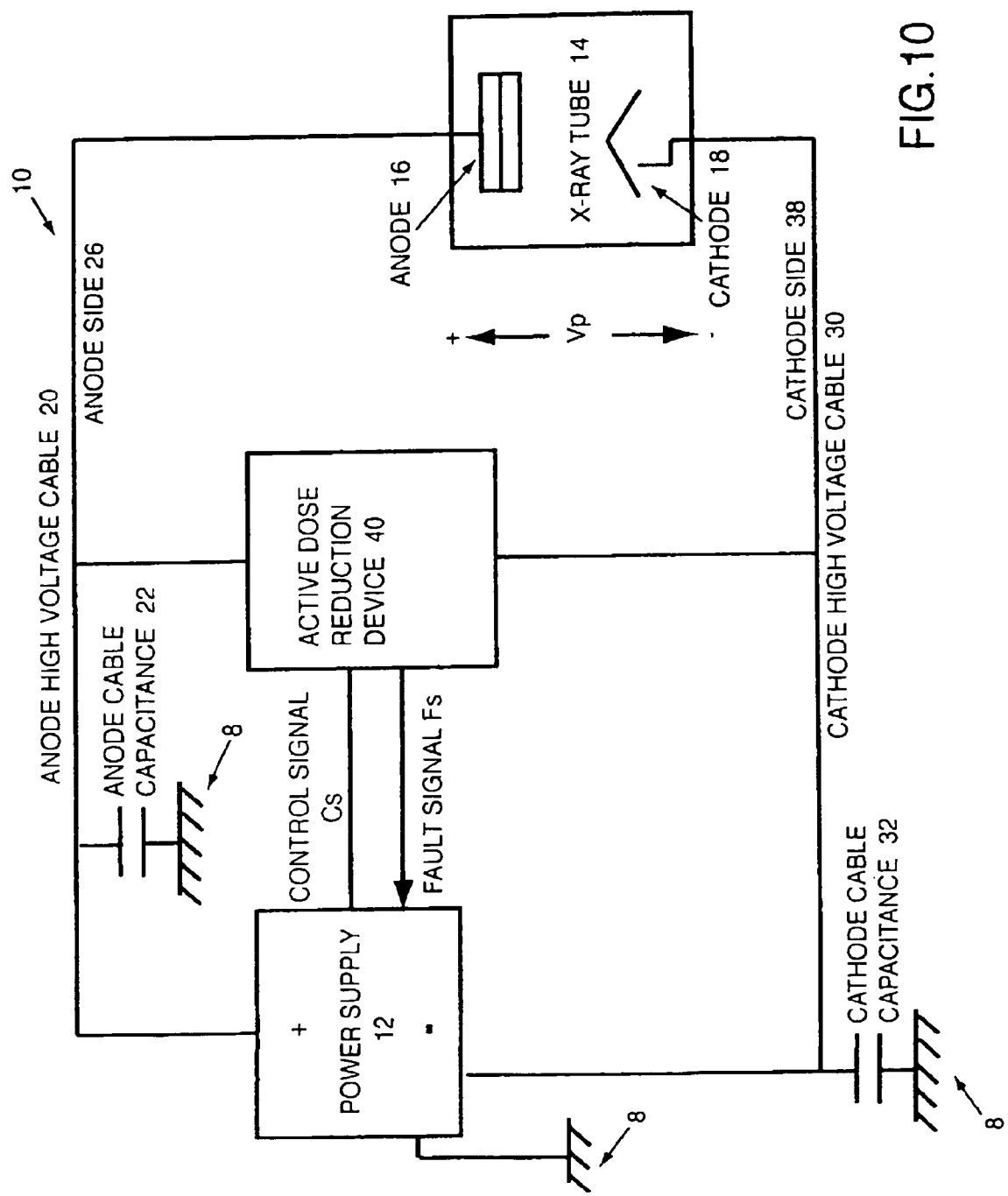
FIG. 10 illustrates a schematic diagram of the present invention according to a still further embodiment.

FIG. 10 illustrates an alternate embodiment according to one preferred embodiment of the present invention where the active dose reduction device 40, rather than connect one component of the imaging system 10 to ground, operatively connects an anode side 26 of one component of the imaging system 10 to the cathode side 38 of the one component and/or of another component of the system 10. For instance, as illustrated in FIG. 10, the active dose reduction device 40 connects the anode high voltage cable 20 to the cathode high voltage cable 30. In this way, upon receipt of the control signal CS, the cells 100 in the active dose reduction device 40 will begin to change from the first state to the second state thereby permitting current to flow from at least one component of the imaging system 10. However, rather than the current flowing from the component of the imaging system 10 to ground 8, current will flow from the anode side 26 to the cathode side 38. It is understood the active dose reduction device 40 may also be connected across any component of the cathode side 38 to any component of the anode side 26.

As illustrated above, the active dose reduction device 40 need not discharge all of the stored energy 22, 32 in the system 10. Rather, sufficient energy such that the voltage differential across the anode 16 and cathode 18 of the x-ray tube 14 will not be sufficient to generate significant x-rays, or, more preferably, will not be sufficient to generate x-rays having a peak energy level above any filters 15 across the x-ray tube 14.

It is understood that the active dose reduction device 40 illustrated in FIG. 10 may be any type of active dose reduction device 40 used for this purpose. In a preferred embodiment, the active dose reduction device 40 will comprise a plurality of cells connecting the anode side 26 to the cathode side 30 of the system 10. In this preferred embodiment, an overvoltage circuit 145 preferably causes a first cell 101 to change from the first state to the second state thereby causing successive cells 100 to change from the first state to the second state through a cascading effect as discussed above. The principal difference would be the first cell may not be connected to ground 8, but may be the first cell in the series closest to the anode side 26 or the cathode side 38 or indeed anywhere in the series of cells 100. The overvoltage circuit 145 will preferably create a voltage pulse which increases the corresponding voltage present from the predetermined Vp across the corresponding cells 100. In a preferred embodiment, two overvoltage circuits 145, one on the anode side 26 and one on the cathode side 38, may work together creating voltage pulses in opposite polarities to commence a cascading effect from both the anode side 26 and the cathode side 38 of the plurality of cells 100.

As discussed above, the active dose reduction device 40 in FIG. 10 may still comprise an ADR current detection device 130 for detecting the presence of current I through at least one of the plurality of cells. Presence or absence of current will then generate a fault signal FS as discussed above. The current I may be the current passing through any one or all of cells 100.

It is understood that the x-ray imaging system in which the active dose reduction device and method may be used with any type of x-ray imaging system. In particular, while the x-ray imaging system has been described with respect to an imaging system used on humans, it is understood that the x-ray imaging system can be used to image animals, such as in veterinary sciences. Furthermore, it is also understood that the x-ray imaging system in which the device and method of the present invention could be utilized may also include x-ray imaging systems for imaging inanimate objects such as building structures, composite materials and other types of objects where x-ray imaging may be beneficial.

Furthermore, while x-ray imaging has been described in the context of diagnostic procedures, it is understood that the x-ray imaging may not be limited to diagnostic procedures. Rather, the present invention may be used in other procedures including treatments to a patient, such as in non-evasive surgery and other types of treatments.

It is understood that while the present invention has been defined in the context of an active dose reduction device 40 comprising cells 100 having Sidacs S, the invention is not limited to this type of device 40. Rather, other types of active dose reduction devices 40 having these characteristics and which can be used to discharge the energy from only the anode side 26, and more preferably only the cathode side 38, may be used.

It will be understood that, although various features of the invention have been described with respect to one or another of the embodiments of the invention, the various features and embodiments of the invention may be combined or used in conjunction with other features and embodiments of the invention as described and illustrated herein.

Although this disclosure has described and illustrated certain preferred embodiments of the invention, it is to be understood that the invention is not restricted to these particular embodiments. Rather, the invention includes all embodiments, which are functional, electrical or mechanical equivalents of the specific embodiments and features that have been described and illustrated herein.

The embodiments of the invention in which an exclusive property or privilege is claimed are defined as follows:

1. An x-ray imaging system comprising:
   an x-ray tube which generates x-rays for x-ray imaging when a pre-selected voltage is supplied thereto;
   a power supply for supplying power to the x-ray tube at the pre-selected voltage;
   a cable set comprising an anode cable and a cathode cable for operatively connecting the power supply to the x-ray tube;
   a plurality of electronic cells, each cell having a first state which prevents flow of current upto a threshold voltage and a second state which permits flow of current, each cell comprising at least one overvoltage device having only two terminals, each cell comprising said cells operatively connected to at least one component of the x-ray imaging system, said component selected from the group comprising the x-ray tube, the power supply and the cable set, such that said plurality of cells prevent current flow to ground when in the first state and permit current flow from the at least one component when in the first state and permit current flow from the at least one component when in the second state;
   an overvoltage circuit to cause at least a first cell of the plurality of electronic cells to exceed the threshold voltage and change from the first state to the second state; and
   wherein while the power supply supplies power to the x-ray tube at the pre-selected voltage, the cells in the first state prevent current flow from the at least one component, and, upon terininanon of the power supply supplying power to the x-ray tube at the pre-selected voltage, the overvoltage circuit causes at least the first cell of the plurality of cells to change from the first state to the second state which causes successive cells to change from the first state to the second state to permit current to flow from the at least one component thereby reducing the x-rays generated by the x-ray tube.

2. The x-ray imaging system as defined in claim 1, wherein each cell in the plurality of cells changes from the second state to the first state once the current passing through the plurality of cells decreases below a threshold current; and wherein after sufficient stored energy in the x-ray imaging system is discharged, the current passing through the plurality of cells decreases below the threshold current to cause the plurality of cells to change from the second state to the first state such that the plurality of cells prevent current flow from the at least one component to ground.

3. The x-ray imaging system as defined in claim 2, wherein the threshold voltage for each cell is approximately equal and the threshold current for each cell is approximately equal.

4. The x-ray imaging system as defined in claim 1, wherein the at least one component of the x-ray system is the cable set only; and
wherein said plurality of cells operatively connect the cable set to ground by operatively connecting either the anode cable to ground, or, the cathode cable to ground, or both the anode cable to ground and the cathode cable to ground.

5. The x-ray imaging system as defined in claim 4, wherein said plurality of cells are arranged in series between either the anode cable and ground or the cathode cable and ground but not both the anode cable to ground and cathode cable to ground.

6. The x-ray imaging system as defined in claim 1, wherein the first cell changing from the first state to the second state causes a cascading effect which successively changes each of the cells of the plurality of cells to the second state.

7. The x-ray imaging system as defined in claim 1, wherein the overvoltage circuit causes at least the first cell to exceed the threshold voltage and change from the first state to the second state in response to a command signal from the power supply indicating tennination of the pre-selected voltage.

8. The x-ray imaging system as defined in claim 1, wherein the threshold voltage for each cell is approximately equal.

9. The x-ray imaging system as defined in claim 1, wherein when the cells are in the first state, the pre-selected voltage creates a voltage potential across corresponding cells, and, the number of cells in the plurality of cells and the threshold voltage of the cells is selected such that the threshold voltage of each of the cells in the plurality of cells is in excess of the voltage potential across the corresponding cell created by the pre-selected voltage; and
wherein the overvoltage circuit comprises a voltage pulse source for selectively supplying a voltage pulse to the first cell which is summed with the voltage across the first cell created by the pre-selected voltage, the voltage pulse being of sufficient magnitude that the voltage sum across the first cell exceeds the threshold voltage for the first cell causing the first cell to move from the first state to the second state thereby permitting the flow of current through the first cell.

10. The x-ray imaging system as defined in claim 9, wherein after the first cell moves from the first state to the second state, the voltage potential across corresponding cells created by the pre-selected voltage increases; and
wherein the voltage pulse is of sufficient magnitude that the voltage sum across a cell immediately adjacent the first cell exceeds its threshold voltage causing the cell immediately adjacent the first cell to move from the first state to the second state.

11. The x-ray imaging system as defined in claim 10 wherein as each cell in the plurality of cells moves from the first state to the second state, the voltage potential created by the pre-selected voltage across corresponding cells remaining in the first state increases until the voltage potential across the corresponding cells in the first state created by the pre-selected voltage exceeds the threshold voltage of the cells remaining in the first state and current is permitted to flow through the cells in the second state from the at least one component to ground.

12. The x-ray imaging system as defined in claim 1, further comprising a fault current detection device for detecting presence of an x-ray reduction current from the at least one component through at least one cell of the plurality of cells;
wherein the fault current detection device sends a fault signal to stop the power supply from supplying power to the x-ray tube if the x-ray reduction current is present before the command signal is sent or the x-ray reduction current is not present after the command signal is sent.

13. The x-ray imaging system as defined in claim 1, wherein the overvoltage devices have a first state which is substantially non-conductive and a second state which is highly conductive, wherein the overvoltage devices electronically change from the first state to the second state when overvoltaged beyond a pre-determined threshold voltage.

14. The x-ray imaging system as defined in claim 13, wherein at least one cell comprises more than one overvoltage device.

15. The x-ray imaging system as defined in claim 13, wherein the two terminal overvoltage devices comprises silicon control rectifiers.

16. The x-ray imaging system as defined in claim 1 wherein the x-ray system has an anode side, which has a positive voltage with respect to ground, and, a cathode side, which has a negative voltage with respect to ground; and
wherein said plurality of cells operatively connect only the cathode side to ground or the anode side to ground, or the cathode side to the anode side.

17. The x-ray imaging system as defined in claim 1 wherein the plurality of cells operatively connect an anode side of the at least one component of the x-ray imaging system to a cathode side of the at least one component of the x-ray imaging system; and
wherein while the power supply supplies power to the x-ray tube at the pre-selected voltage, the cells in the first state prevent current flow from the cathode side of the at least one component to the anode side of the at least one component, and, upon termination of the power supply supplying power to the x-ray tube at the pre-selected voltage, the overvoltage circuit causes at least the first cell of the plurality of cells to change from the first state to the second state which causes successive cells to change from the first state to the second state to permit current to flow from the cathode side of the at least one component to the anode side of the at least one component thereby reducing the x-rays generated by the x-ray tube.

18. A device for reducing x-ray dosage from an x-ray imaging system, said device comprising:
a plurality of electronic cells, each cell having a first state which prevents flow of current upto a threshold voltage and a second state which permits flow of current, each cell comprising at least one overvoltage device having only two terminals, said plurality of electronic cells operatively connected to at least one component of the x-ray imaging system such that, when each of the plurality of cells is in the first state, the voltage differential between across the plurality of cells is insufficient to surpass the threshold voltage of any one cell of the plurality of cells;

a voltage pulse source for generating a voltage pulse of sufficient magnitude to cause at least a first cell of the plurality of electronic cells to exceed the threshold voltage;

wherein substantially simultaneously with the terinination of an x-ray imaging exposure, the voltage pulse source causes a first cell of the plurality of cells to exceed its threshold voltage changing the first cell from the first state to the second state; and wherein the first cell changing from the first state to the second state causes the plurality of cells to change from the first state to the second state permitting discharge of stored energy in the at least one component of the imaging system to ground to reduce the x-ray dosage from the imaging system.

19. A device for reducing x-ray dosage from an imaging system as defined in claim 18, wherein the first cell changing from the first state to the second state causes a cascading effect which successively changes each of the cells of the plurality of cells to the second state.

20. A device for reducing x-ray dosage from an imaging system as defined in claim 18 wherein each cell in the plurality of cells changes from the second state to the first state once the current passing through the plurality of cells decreases below a threshold current; and wherein after sufficient stored energy in the x-ray imaging system is discharged, the current passing through the plurality of cells decreases below the threshold current to cause the plurality of cells to change from the second state to the first state such that the plurality of cells prevent current flow from the at least one component to ground.

21. A device for reducing x-ray dosage from an imaging system as defined in claim 18, wherein the x-ray system has an anode side, which has a positive voltage with respect to ground, and, a cathode side, which has a negative voltage with respect to ground, and wherein said plurality of cells operatively connect only the cathode side to ground or the anode side to ground, or the cathode side to the anode side.

22. A method for reducing an active dose of x-rays during x-ray imaging, said method comprising:

applying a pre-selected voltage through a cable set, said cable set including an anode cable and a cathode cable operatively connecting a power supply to an x-ray tube, said pre-selected voltage being sufficient to cause the x-ray tube to generate x-rays for x-ray imaging;

upon termination of the pre-selected voltage, over voltaging a first cell of a purality of cells operatively connecting at least one of the cable set or the x-ray tube to ground, each cell in said plurality of cells having a first state which prevents flow of current until overvoltaged and a second state which pennits flow of current each cell also comprising at least one overvoltage device having only two terminals;

wherein over voltaging the first cell of the plurality of cells causes each of the remaining plurality of cells to become overvoltaged whereby stored energy in at least one of the x-ray tube, the anode cable and the cathode cable are discharged to ground thereby decreasing the x-rays generated by the x-ray tube upon termination of the pre-selected voltage.

\* \* \* \* \*